(12) United States Patent
Hosoumi et al.

(10) Patent No.: US 10,586,932 B2
(45) Date of Patent: Mar. 10, 2020

(54) LIGHT-EMITTING ELEMENT, LIGHT-EMITTING DEVICE, DISPLAY DEVICE, ELECTRONIC DEVICE, AND LIGHTING DEVICE

(71) Applicant: Semiconductor Energy Laboratory Co., Ltd., Kanagawa-ken (JP)

(72) Inventors: Shunsuke Hosoumi, Kanagawa (JP); Tatsuyoshi Takahashi, Kanagawa (JP); Takahiro Ishisone, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 15/166,585

(22) Filed: May 27, 2016

(65) Prior Publication Data

US 2016/0351829 A1 Dec. 1, 2016

(30) Foreign Application Priority Data

May 29, 2015 (JP) .................................. 2015-109756

(51) Int. Cl.
*H01L 51/00* (2006.01)
*C07D 491/048* (2006.01)
(Continued)

(52) U.S. Cl.
CPC ...... *H01L 51/0072* (2013.01); *C07D 491/048* (2013.01); *C07D 495/04* (2013.01);
(Continued)

(58) Field of Classification Search
CPC combination set(s) only.
See application file for complete search history.

(56) References Cited

U.S. PATENT DOCUMENTS 7,175,922 B2 2/2007 Jarikov et al.
7,183,010 B2 2/2007 Jarikov
(Continued)

FOREIGN PATENT DOCUMENTS

CN 105103327 A 11/2015
EP 1 202 608 A2 5/2002
(Continued)

OTHER PUBLICATIONS

Seo S. et al., Japanese Journal of Applied Physics, vol. 53, No. 4, p. 042102, Mar. 17, 2014.*
(Continued)

*Primary Examiner* — Jennifer A Chriss
*Assistant Examiner* — Sean M DeGuire
(74) *Attorney, Agent, or Firm* — Husch Blackwell LLP

(57) ABSTRACT

A light-emitting element having high emission efficiency is provided. A light-emitting element which has high emission efficiency without using a rare metal as a light-emitting material is provided. A light-emitting element includes a first electrode, a second electrode, and a layer between the first electrode and the second electrode. The layer contains a first organic compound and a second organic compound. The second organic compound has a carbazole skeleton and a substituted or unsubstituted bivalent aromatic hydrocarbon group. The second organic compound further has a benzofuropyrimidine skeleton or a benzothienopyrimidine skeleton. The aromatic hydrocarbon group is bonded to the carbazole skeleton. The aromatic hydrocarbon group is bonded to the benzofuropyrimidine skeleton or the benzothienopyrimidine skeleton. The first organic compound and the second organic compound can form an exciplex.

32 Claims, 15 Drawing Sheets

(51) Int. Cl.
  *C07D 495/04* (2006.01)
  *C09K 11/06* (2006.01)
  *C09K 11/02* (2006.01)
  *H01L 51/50* (2006.01)

(52) U.S. Cl.
  CPC ............ *C09K 11/025* (2013.01); *C09K 11/06* (2013.01); *H01L 51/0051* (2013.01); *H01L 51/0071* (2013.01); *C09K 2211/1007* (2013.01); *C09K 2211/1048* (2013.01); *C09K 2211/1051* (2013.01); *H01L 51/5012* (2013.01)

(56) References Cited

U.S. PATENT DOCUMENTS

| | | |
|---|---|---|
| 7,332,857 B2 | 2/2008 | Seo et al. |
| 7,597,967 B2 | 10/2009 | Kondakova et al. |
| 7,993,760 B2 | 8/2011 | Komori et al. |
| 8,034,465 B2 | 10/2011 | Liao et al. |
| 8,274,214 B2 | 9/2012 | Ikeda et al. |
| 8,586,204 B2 | 11/2013 | Xia et al. |
| 8,652,652 B2 | 2/2014 | Brooks et al. |
| 8,822,708 B2 | 9/2014 | Ma et al. |
| 8,853,680 B2 | 10/2014 | Yamazaki et al. |
| 8,866,377 B2 | 10/2014 | Adamovich et al. |
| 8,963,127 B2 | 2/2015 | Pieh et al. |
| 8,981,355 B2 | 3/2015 | Seo |
| 8,993,129 B2 | 3/2015 | Endo et al. |
| 8,994,263 B2 | 3/2015 | Shitagaki et al. |
| 9,054,317 B2 | 6/2015 | Monkman et al. |
| 9,123,903 B2 | 9/2015 | Lin et al. |
| 9,153,786 B2 | 10/2015 | Ma et al. |
| 9,159,942 B2 | 10/2015 | Seo et al. |
| 9,175,213 B2 | 11/2015 | Seo et al. |
| 9,356,250 B2 | 5/2016 | Ohsawa et al. |
| 9,604,928 B2 | 3/2017 | Shitagaki et al. |
| 2003/0175553 A1 | 9/2003 | Thompson et al. |
| 2005/0048310 A1 | 3/2005 | Cocchi et al. |
| 2005/0221116 A1 | 10/2005 | Cocchi et al. |
| 2006/0134464 A1 | 6/2006 | Nariyuki |
| 2007/0090756 A1 | 4/2007 | Okada et al. |
| 2008/0314965 A1 | 12/2008 | Roberts et al. |
| 2009/0153034 A1 | 6/2009 | Lin et al. |
| 2012/0217487 A1 | 8/2012 | Yamazaki et al. |
| 2013/0277656 A1* | 10/2013 | Seo ............... H01L 51/5016 257/40 |
| 2014/0034929 A1* | 2/2014 | Hamada ........... H01L 51/5016 257/40 |
| 2014/0034932 A1 | 2/2014 | Seo et al. |
| 2014/0042413 A1 | 2/2014 | Xia et al. |
| 2014/0103327 A1 | 4/2014 | Brooks et al. |
| 2014/0291643 A1* | 10/2014 | Ogita ............... H01L 51/0074 257/40 |
| 2014/0291645 A1 | 10/2014 | Inoue et al. |
| 2014/0319492 A1 | 10/2014 | Seo et al. |
| 2015/0001524 A1 | 1/2015 | Brooks et al. |
| 2015/0069352 A1 | 3/2015 | Kim et al. |
| 2015/0243893 A1 | 8/2015 | Joseph et al. |
| 2015/0372243 A1 | 12/2015 | Ma et al. |
| 2016/0013421 A1 | 1/2016 | Inoue et al. |
| 2016/0351826 A1* | 12/2016 | Kim ............... C07D 495/04 |

FOREIGN PATENT DOCUMENTS

| | | |
|---|---|---|
| EP | 2 910 555 A1 | 8/2015 |
| JP | 06-220059 A | 8/1994 |
| JP | 2008-288344 A | 11/2008 |
| JP | 2011-084531 A | 4/2011 |
| JP | 2011084531 A * | 4/2011 |
| JP | 2014-192214 A | 10/2014 |
| JP | 2014-208621 A | 11/2014 |
| JP | 2014-209611 A | 11/2014 |
| JP | 2015-134745 A | 7/2015 |
| JP | 2015-157808 A | 9/2015 |
| JP | 2016-028421 A | 2/2016 |
| KR | 2015-0100555 A | 9/2015 |
| KR | 2015-0132837 A | 11/2015 |
| KR | 2015-0135289 A | 12/2015 |
| KR | 2016-0007380 A | 1/2016 |
| TW | 201443058 | 11/2014 |
| TW | 201504219 | 2/2015 |
| TW | 201527302 | 7/2015 |
| WO | WO 2014/065073 A1 | 5/2014 |
| WO | WO 2014/157018 A1 | 10/2014 |
| WO | WO 2014/157599 A1 | 10/2014 |
| WO | WO 2015/037675 A1 | 3/2015 |
| WO | WO 2016/193845 A1 | 12/2016 |

OTHER PUBLICATIONS

Machine Translation of JP 2011084531 generated on May 23, 2017.*

International Search Report re Application No. PCT/IB2016/052839, dated Aug. 30, 2016.

Written Opinion re Application No. PCT/IB2016/052839, dated Aug. 30, 2016.

Zhao, Y. et al., "Synthesis, X-ray Structure and Antitumor Activity of 4-(1,3,4-thiadiazole-2-ylthio)benzo[4,5]furo[3,2-d]pyrimidine Derivatives," Chinese Journal of Organic Chemistry, 2010, vol. 30, No. 7, pp. 1093-1097.

Goled, S.N. et al., "Synthesis and Reactions of 2-Substituted 4-Hydrazinobenzofuro [3,2-d] Pyrimidines and Their Antibacterial Activity," Oriental Journal of Chemistry, 1997, vol. 13, No. 1, pp. 73-75.

Tolkunov, S.V. et al., "Synthesis and Reactions of 2,4-Disubstituted Benzo[b]furano, Benzo[b]thieno and Indolo[3,2-d]-1,3-Oxazinium Salts," Chemistry of Heterocyclic Compounds, 1990, vol. 26, No. 11, pp. 1310-1312.

Goushi, K. et al., "Efficient Organic Light-Emitting Diodes Through Up-Conversion from Triplet to Singlet Excited States of Exciplexes," Applied Physics Letters, Jul. 12, 2012, vol. 101, No. 2, pp. 023306-1-023306-4.

Yersin, H. et al., *Highly Efficient OLEDs with Phosphorescent Materials*, 2008, pp. 1-97,283-309, Wiley-VCH Verlag GmbH & Co.

Tokito,S. et al., "Improvement in Performance by Doping," Organic EL Display, Aug. 20, 2004, pp. 67-99, Ohmsha.

Jeon, W.S. et al., "Ideal Host and Guest System in Phosphorescent OLEDs," Organic Electronics, 2009, vol. 10, pp. 240-246, Elsevier.

Su, S-J et al., "RGB Phosphorescent Organic Light-Emitting Diodes by Using Host Materials with Heterocyclic Cores:Effect of Nitrogen Atom Orientations," Chemistry of Materials, 2011, vol. 23, No. 2, pp. 274-284.

Rausch, A.F. et al., "Matrix Effects on the Triplet State of the OLED Emitter Ir(4,6-dFppy)2(pic)(Flrpic):Investigations by High-Resolution Optical Spectroscopy," Inorganic Chemistry, 2009, vol. 48, No. 5, pp. 1928-1937.

Gong, X. et al., "Phosphorescence from Iridium Complexes Doped into Polymer Blends," Journal of Applied Physics, Feb. 1, 2004, vol. 95, No. 3, pp. 948-953.

Zhao, Q. et al., "Synthesis and Photophysical, Electrochemical, and Electrophosphorescent Properties of a Series of Iridium(III) Complexes Based on Quinoline Derivatives and Different β-Diketonate Ligands," Organometallics, Jun. 14, 2006, vol. 25, No. 15, pp. 3631-3638.

Hino, Y. et al., "Red Phosphorescent Organic Light-Emitting Diodes Using Mixture System of Small-Molecule and Polymer Host," Japanese Journal of Applied Physics, Apr. 21, 2005, vol. 44, No. 4B, pp. 2790-2794.

Tsuboyama, A. et al., "Homoleptic Cyclometalated Iridium Complexes with Highly Efficient Red Phosphorescence and Application to Organic Light-Emitting Diode," Journal of the American Chemical Society, 2003, vol. 125, No. 42, pp. 12971-12979.

Kondakova, M.E. et al., "High-Efficiency, Low-Voltage Phosphorescent Organic Light-Emitting Diode Devices with Mixed Host," Journal of Applied Physics, Nov. 4, 2008, vol. 104, pp. 094501-1-094501-17.

(56) References Cited

OTHER PUBLICATIONS

Chen, F-C. et al., "Triplet Exciton Confinement in Phosphorescent Polymer Light-Emitting Diodes," Applied Physics Letters, Feb. 17, 2003, vol. 82, No. 7, pp. 1006-1008.
Lee, J.Y. et al., "Stabilizing the Efficiency of Phosphorescent Organic Light-Emitting Diodes," SPIE Newsroom, Apr. 21, 2008, pp. 1-3.
Tokito, S. et al., "Confinement of Triplet Energy on Phosphorescent Molecules for Highly-Efficient Oragnic Blue-Light-Emitting Devices," Applied Physics Letters, Jul. 21, 2003, vol. 83, No. 3, pp. 569-571.
Endo, A. et al., "Efficient Up-Conversion of Triplet Excitons Into a Singlet State and Its Application for Organic Light Emitting Diodes," Applied Physics Letters, Feb. 24, 2011, vol. 98, No. 8, pp. 083302-1-083302-3.
Itano, K. et al., "Exclplex Formation at the Organic Solid-State Interface: Yellow Emission in Organic Light-Emitting Diodes Using Green-Fluorescent tris(8-quinolinolato)aluminum and Hole-Transporting Molecular Materials with Low Ionization Potentials," Applied Physics Letters, Feb. 9, 1998, vol. 72, No. 6, pp. 636-638.
Park, Y-S. et al., "Efficient Triplet Harvesting by Fluorescent Molecules Through Exciplexes for High Efficiency Organic Light-Emitting Diodes," Applied Physics Letters, Apr. 18, 2013, vol. 102, No. 15, pp. 153306-1-153306-5.

\* cited by examiner

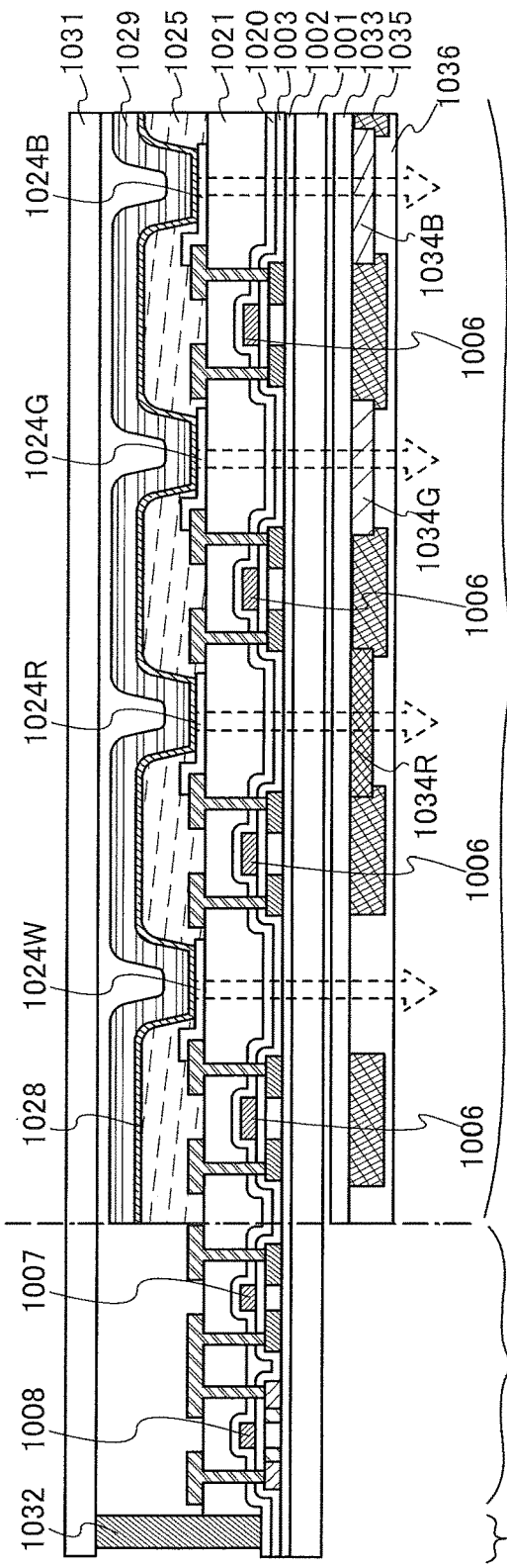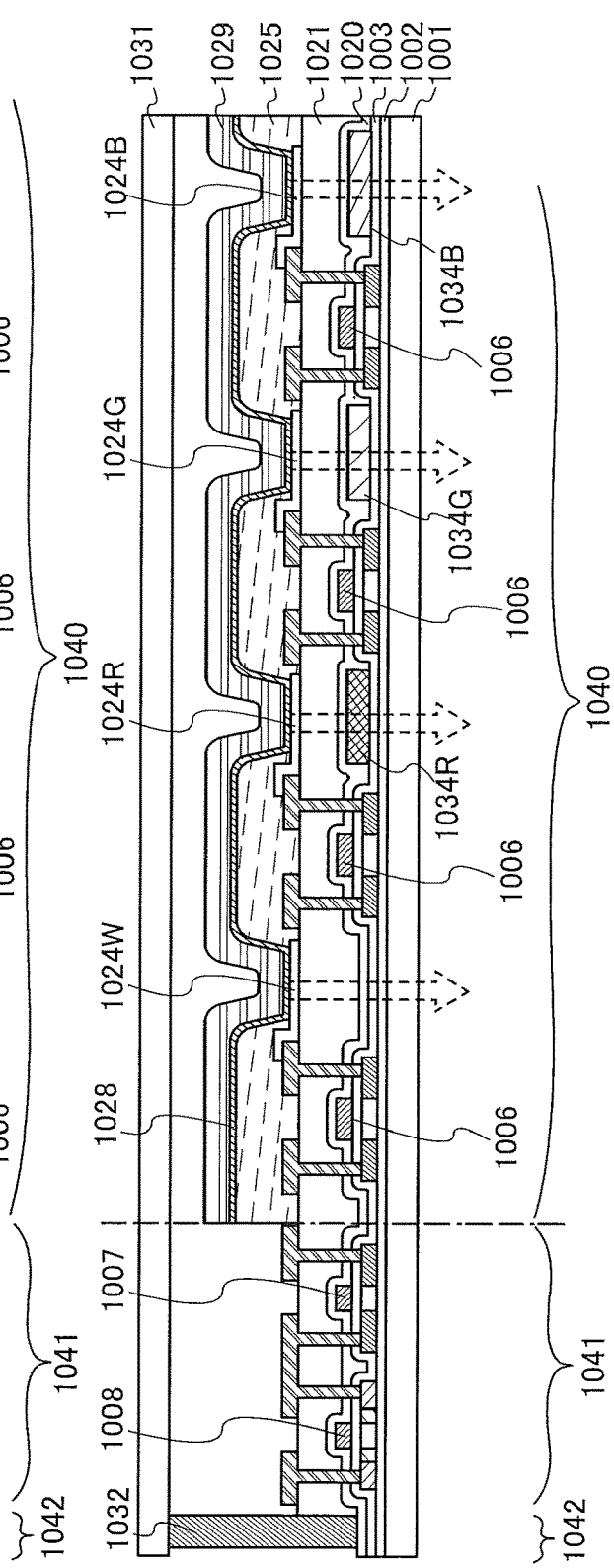
FIG. 3A
FIG. 3B

LIGHT-EMITTING ELEMENT, LIGHT-EMITTING DEVICE, DISPLAY DEVICE, ELECTRONIC DEVICE, AND LIGHTING DEVICE

TECHNICAL FIELD

One embodiment of the present invention relates to a compound having a benzofuropyrimidine skeleton or a benzothienopyrimidine skeleton, in addition to a carbazole skeleton. One embodiment of the present invention relates to a light-emitting element in which a light-emitting layer capable of providing light emission by application of an electric field is provided between a pair of electrodes, and also relates to a display device, an electronic device, a semiconductor device, and a lighting device each including the light-emitting element.

Note that one embodiment of the present invention is not limited to the above technical field. One embodiment of the present invention relates to an object, a method, and a manufacturing method. In addition, one embodiment of the present invention relates to a process, a machine, manufacture, or a composition of matter. In particular, one embodiment of the present invention relates to a semiconductor device, a display device, a light-emitting device, a lighting device, driving methods thereof, or manufacturing methods thereof.

BACKGROUND ART

Advances are being made in application of a current excitation type light-emitting element in which an organic compound is used as a light-emitting substance, i.e., an organic EL element, to light sources, lighting, displays, and the like.

As is known, in an organic EL element, the generation ratio of excitons in a singlet excited state to excitons in a triplet excited state is 1:3. Thus, the limit value of internal quantum efficiency of fluorescence, which is emitted by conversion of a singlet excited state into light emission, is 25%, while phosphorescence, which is emitted by conversion of a triplet excited state into light emission, can have an internal quantum efficiency of 100% when energy transfer via intersystem crossing from a singlet excited state is taken into account. In view of the above, an organic EL element (also referred to as a phosphorescent light-emitting element) in which a phosphorescent material is used as a light-emitting substance is selected in many cases so that light is emitted efficiently.

Most of the substances capable of efficiently converting a triplet excited state into light emission are organometallic complexes, and in most cases, central metals of the organometallic complexes are rare metals whose production is small. The price of rare metals is high and greatly fluctuates, and supply thereof might be unstable depending on the global situation. For this reason, there are some concerns about cost and supply regarding phosphorescent light-emitting elements.

To cause conversion of a triplet excited state into light emission, delayed fluorescence can also be utilized. In this case, not phosphorescence but fluorescence is obtained because reverse intersystem crossing from a triplet excited state to a singlet excited state is utilized and the light emission occurs from a singlet excited state. This is readily caused when an energy difference between a singlet excited state and a triplet excited state is small. Emission efficiency exceeding the theoretical limit of emission efficiency of fluorescence has been actually reported.

It has also been reported that an exciplex (excited complex) formed by two kinds of substances was utilized to achieve a state where an energy difference between a singlet excited state and a triplet excited state is small, whereby a high-efficiency light-emitting element was provided.

REFERENCE

Non-Patent Document

[Non-Patent Document 1] K. Goushi et al., *Applied Physics Letters*, 101, pp. 023306/1-023306/4 (2012).

DISCLOSURE OF INVENTION

However, in such a light-emitting element utilizing an exciplex, use of certain substances often prevents efficient light emission. Actually, in the history of development of organic EL elements, an exciplex has been considered to decrease efficiency and organic EL elements have been generally designed such that an exciplex is not formed.

In view of the above, an object of one embodiment of the present invention is to provide a light-emitting element which has high emission efficiency. Another object of one embodiment of the present invention is to provide a light-emitting element which has high emission efficiency without using a rare metal as a light-emitting material. A further object of one embodiment of the present invention is to provide a light-emitting element which utilizes an exciplex and has high efficiency. A still further object of one embodiment of the present invention is to provide a light-emitting element which emits light from an exciplex and has high efficiency.

A yet still further object of one embodiment of the present invention is to provide a light-emitting device, a display device, an electronic device, and a lighting device each of which has high emission efficiency by using any of the above light-emitting elements.

Note that the descriptions of these objects do not disturb the existence of other objects. In one embodiment of the present invention, there is no need to achieve all the objects. Other objects will be apparent from and can be derived from the description of the specification, the drawings, the claims, and the like.

One embodiment of the present invention is a light-emitting element including a first electrode, a second electrode, and a layer between the first electrode and the second electrode. The layer contains a first organic compound and a second organic compound. The second organic compound has a carbazole skeleton and a substituted or unsubstituted bivalent aromatic hydrocarbon group, and further has a benzofuropyrimidine skeleton or a benzothienopyrimidine skeleton. The aromatic hydrocarbon group is bonded to the carbazole skeleton, and is bonded to the benzofuropyrimidine skeleton or the benzothienopyrimidine skeleton. The first organic compound and the second organic compound can form an exciplex.

Another embodiment of the present invention is a light-emitting element including a first electrode, a second electrode, and a layer between the first electrode and the second electrode. The layer contains a first organic compound and a second organic compound. The second organic compound has a carbazole skeleton and a substituted or unsubstituted bivalent aromatic hydrocarbon group, and further has a benzofuro[3,2-d]pyrimidine skeleton or a benzothieno[3,2- d]pyrimidine skeleton. The aromatic hydrocarbon group is bonded to the carbazole skeleton, and is bonded to the benzofuro[3,2-d]pyrimidine skeleton or the benzothieno[3,2-d]pyrimidine skeleton. The first organic compound and the second organic compound can form an exciplex.

Note that in the light-emitting element of one embodiment of the present invention, the 4-position of the benzofuro[3,2-d]pyrimidine skeleton or the benzothieno[3,2-d]pyrimidine skeleton may be bonded to the aromatic hydrocarbon group. In the light-emitting element of one embodiment of the present invention, the 4-position of the benzofuro[3,2-d]pyrimidine skeleton or the benzothieno[3,2-d]pyrimidine skeleton may be bonded to the aromatic hydrocarbon group while the other positions may be unsubstituted. In the light-emitting element of one embodiment of the present invention, the 9-position of the carbazole skeleton may be bonded to the aromatic hydrocarbon group. In the light-emitting element of one embodiment of the present invention, the aromatic hydrocarbon group may have 6 to 60 carbon atoms. In the light-emitting element of one embodiment of the present invention, the aromatic hydrocarbon group may have 6 to 13 carbon atoms. In the light-emitting element of one embodiment of the present invention, the aromatic hydrocarbon group may have a biphenyldiyl group. In the light-emitting element of one embodiment of the present invention, the biphenyldiyl group may be a 3,3'-biphenyldiyl group.

In the light-emitting element of one embodiment of the present invention, the second organic compound may be an organic compound represented by a structural formula (100).

[Chemical formula 1]

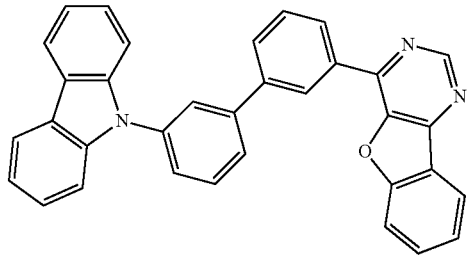

(100)

In the light-emitting element of one embodiment of the present invention, the second organic compound may be an organic compound represented by a structural formula (200).

[Chemical formula 2]

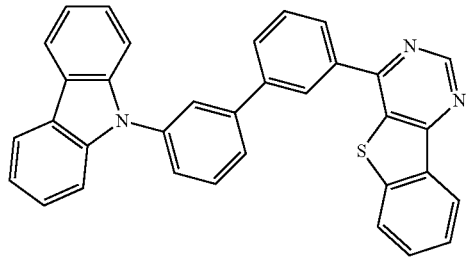

(200)

In the light-emitting element of one embodiment of the present invention, the second organic compound may have an electron-transport property and the first organic compound may have a hole-transport property. In the light-emitting element of one embodiment of the present invention, the first organic compound may be an aromatic amine. In the light-emitting element of one embodiment of the present invention, the triplet excitation energy levels of the first organic compound and the second organic compound may be higher than the triplet excitation energy level of the exciplex. In the light-emitting element of one embodiment of the present invention, light emission may include a delayed fluorescence component.

Another embodiment of the present invention is a lighting device including the light-emitting element of one embodiment of the present invention and a switch. Another embodiment of the present invention is a light-emitting device including the light-emitting element of one embodiment of the present invention and a unit for controlling the light-emitting element. Another embodiment of the present invention is a display device including the light-emitting element of one embodiment of the present invention in a display portion and a unit for controlling the light-emitting element. Another embodiment of the present invention is an electronic device including the light-emitting element of one embodiment of the present invention and a switch.

In one embodiment of the present invention, a light-emitting element which has high emission efficiency can be provided. In one embodiment of the present invention, a light-emitting element which has high emission efficiency without using a rare metal as a light-emitting material can be provided. In one embodiment of the present invention, a light-emitting element which utilizes an exciplex and has high efficiency can be provided. In one embodiment of the present invention, a light-emitting element which emits light from an exciplex and has high efficiency can be provided.

Note that the description of these effects does not disturb the existence of other effects. One embodiment of the present invention does not necessarily achieve all the effects listed above. Other effects will be apparent from and can be derived from the description of the specification, the drawings, the claims, and the like.

BRIEF DESCRIPTION OF DRAWINGS

In the accompanying drawings:

FIGS. 3A and 3B are conceptual diagrams of active matrix light-emitting devices;

FIGS. 7A, 7B1, 7B2, 7C, and 7D illustrate electronic devices;

BEST MODE FOR CARRYING OUT THE INVENTION

Figure 1A:
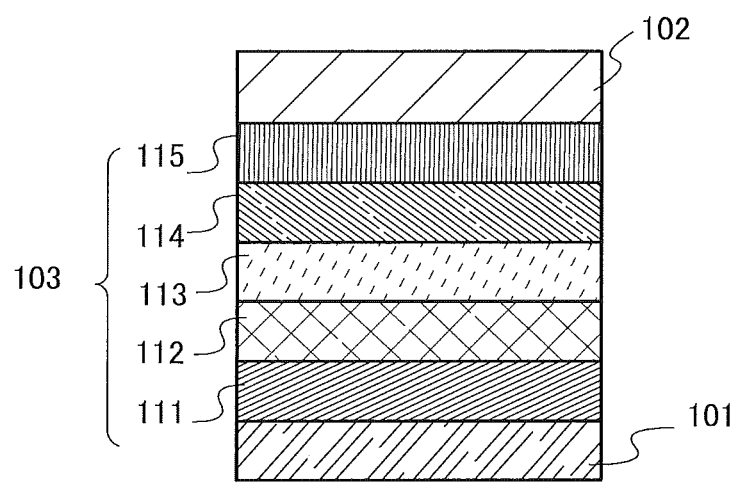
FIGS. 1A and 1B are conceptual diagrams of light-emitting elements.

Hereinafter, embodiments of the present invention will be described. Note that the present invention can be implemented in various modes, and it is easily understood by those skilled in the art that modes and details disclosed herein can be modified in various ways without departing from the spirit and the scope of the present invention. Therefore, the present invention is not interpreted as being limited to the description of the following embodiments.

Note that in each drawing described in this specification, the size, the thickness, and the like of each component such as an anode, a layer containing an organic compound, a charge-generation layer, and a cathode are exaggerated for clarity in some cases. Therefore, the sizes of the components are not limited to the sizes in the drawings and relative sizes between the components.

Ordinal numbers such as "first", "second", and "third" in this specification and the like are used for convenience and do not denote the order of steps or the stacking order of layers. Therefore, for example, description can be made even when "first" is replaced with "second" or "third", as appropriate. In addition, the ordinal numbers in this specification and the like are not necessarily the same as those which specify one embodiment of the present invention.

Note that in the structures of the present invention described in this specification and the like, the same portions or portions having similar functions in different drawings are denoted by the same reference numerals, and description of such portions is not repeated. Further, the same hatching pattern is applied to portions having similar functions, and the portions are not especially denoted by reference numerals in some cases.

In this specification, color is defined by three aspects of hue (corresponding to the wavelength of light of a single color), chroma (saturation, i.e., the degree to which it differs from white), and value (brightness, i.e., the intensity of light). In this specification, color may be defined by only one of the above three aspects or two of the aspects which are selected arbitrarily. In this specification, a difference between two colors of light means a difference in at least one of the above three aspects and includes a difference in the shapes of two spectra of light or in the distributions of the relative intensity of the peaks in the spectra.

Note that the terms "film" and "layer" can be interchanged with each other depending on the case or circumstances. For example, the term "conductive layer" can be changed into the term "conductive film" in some cases, and the term "insulating film" can be changed into the term "insulating layer" in some cases.

Embodiment 1

As a method for converting a triplet excited state into light emission, there are a method utilizing phosphorescence, which is direct emission from a triplet excited state, and a method utilizing delayed fluorescence, which is light emitted from a singlet excited state after a triplet excited state is turned into a singlet excited state via reverse intersystem crossing.

A structure of a light-emitting element that uses a phosphorescent material and emits light with extremely high efficiency has been reported, which actually proves advantages of the utilization of a triplet excited state for light emission. However, central metals of phosphorescent materials are mostly rare metals, and there are concerns about cost and supply in mass production.

Some degree of success in a light-emitting element using a delayed fluorescent material has been achieved in recent years. However, a substance emitting delayed fluorescence with relatively high efficiency has an extremely rare state where a singlet excited state and a triplet excited state are close to each other and accordingly has a unique molecular structure; thus, the kind of such a substance is still limited.

It has been reported that an exciplex (also called excited complex) is a complex in an excited state which is formed by two kinds of molecules due to charge-transfer interaction and that the singlet excited state and the triplet excited state of an exciplex are close to each other in many cases.

Therefore, an exciplex readily emits delayed fluorescence even at room temperature and might allow a fluorescent light-emitting element to have high efficiency. An emission wavelength of light emitted from an exciplex changes in accordance with a difference between a shallower HOMO level and a deeper LUMO level of the two kinds of substances that form the complex. Thus, light with a desired wavelength can be obtained relatively easily by selection of substances forming an exciplex.

However, positive use of light emission from an exciplex is still under investigation. There are few guidelines for selecting substances to achieve high emission efficiency, and without any guideline, a favorable light-emitting element will never be provided.

In view of the above, in this embodiment, a structure of a light-emitting element in which an exciplex is used as an emission center and which emits light with high efficiency is described.

A light-emitting element in this embodiment includes a layer containing an organic compound (the layer may also contain an inorganic compound) between a pair of electrodes, and the layer containing an organic compound includes at least a light-emitting layer. The light-emitting layer contains a first organic compound having a hole-transport property and a second organic compound having an electron-transport property.

A combination of the first organic compound and the second organic compound forms an exciplex when they are excited by a current or when a current flows therein. To form an exciplex, the HOMO level and LUMO level of the first organic compound are preferably shallower than the HOMO level and LUMO level of the second organic compound, respectively.

The formation process of the exciplex is considered to be roughly classified into the following two processes.

One formation process is the process in which an exciplex is formed by the first organic compound having a hole-transport property and the second organic compound having an electron-transport property which are in the state of having carriers (cation or anion).

The other formation process is the process in which one of the first organic compound having a hole-transport property and the second organic compound having an electron-transport property forms a singlet exciton and then the singlet exciton interacts with the other in the ground state to form an exciplex.

The exciplex in this embodiment may be formed by either process.

When the second organic compound having an electron-transport property has a structure in which a carbazole skeleton is bonded to a benzofuropyrimidine skeleton or a benzothienopyrimidine skeleton through a substituted or unsubstituted bivalent aromatic hydrocarbon group, light emission can be efficiently obtained from the exciplex. It is particularly preferable to use the benzofuropyrimidine skeleton to obtain light emission from the light-emitting element more efficiently. Note that the benzofuropyrimidine skeleton is more preferably used in formation of an exciplex than the benzothienopyrimidine skeleton since the LUMO level of the benzofuropyrimidine skeleton is slightly deeper than that of the benzothienopyrimidine skeleton.

As the benzofuropyrimidine skeleton, a benzofuro[3,2-d]pyrimidine skeleton is preferable, and as the benzothienopyrimidine skeleton, a benzothieno[3,2-d]pyrimidine skeleton is preferable. This is because a benzene ring is introduced into the 6-position of pyrimidine in such skeletons, which improves an electron-transport property. Moreover, the LUMO level of each of such skeletons is deeper than that of a pyrimidine skeleton, which is favorable for formation of an exciplex.

It is preferable that the 4-position of the benzofuro[3,2-d]pyrimidine skeleton or the benzothieno[3,2-d]pyrimidine skeleton be bonded to the aromatic hydrocarbon group. In that case, the 4-position and the 6-position of pyrimidine are substituted, whereby the electron-transport property can be increased. Moreover, the LUMO level becomes deeper, which is more favorable for formation of an exciplex.

Furthermore, it is preferable that the 4-position of the benzofuro[3,2-d]pyrimidine skeleton or the benzothieno[3,2-d]pyrimidine skeleton be bonded to the aromatic hydrocarbon group and that the other positions be unsubstituted. When the positions other than 4-position are unsubstituted, the benzofuro[3,2-d]pyrimidine skeleton or the benzothieno[3,2-d]pyrimidine skeleton easily interacts with the first organic compound, whereby an exciplex is easily formed.

As for the carbazole skeleton, the 9-position of the carbazole skeleton is preferably bonded to the aromatic hydrocarbon group. In that case, an electrochemically stable compound can be obtained.

When the carbazole skeleton is bonded to the benzofuropyrimidine skeleton or the benzothienopyrimidine skeleton through the bivalent aromatic hydrocarbon group, formation of an exciplex by the first and second organic compounds is more likely to occur than a charge-transfer excited state in the second organic compound. In other words, when a first skeleton is physically separated from a second skeleton, not HOMO-LUMO intramolecular transition but HOMO-LUMO intermolecular transition (e.g., transition from HOMO of a first organic compound to LUMO of a second organic compound) is more likely to occur.

The bivalent aromatic hydrocarbon group preferably has 6 to 60 carbon atoms. In particular, a bivalent aromatic hydrocarbon group having 6 to 13 carbon atoms is more preferable because of its excellent sublimability. Taking sublimability into account in addition to separation of the carbazole skeleton from the benzofuropyrimidine skeleton or the benzothienopyrimidine skeleton by the bivalent aromatic hydrocarbon group, a biphenyldiyl group is preferable as such an aromatic hydrocarbon group. Specifically, in view of increase in the triplet excited level, a 3,3'-biphenyldiyl group is more preferable. The bivalent aromatic hydrocarbon group is preferably bonded to a nitrogen atom in the carbazole skeleton. When any of these groups includes a substituent, an alkyl group having 1 to 6 carbon atoms and an aryl group having 6 to 12 carbon atoms (e.g., a phenyl group or biphenyldiyl group) are given as examples of the substituent.

The second organic compound can be represented by the following general formula (G1).

[Chemical formula 3]

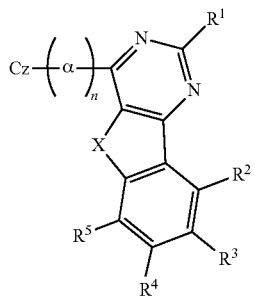

(G1)

In the general formula (G1), each of $R^1$ to $R^5$ independently represents any one of hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, and a substituted or unsubstituted aryl group having 6 to 13 carbon atoms. In addition, ac represents a substituted or unsubstituted aromatic hydrocarbon group, and n is an integer of 1 to 4. Moreover, Cz represents a carbazole skeleton. Furthermore, X represents any one of an oxygen atom and a sulfur atom.

The second organic compound can also be represented by the following general formula (G2).

[Chemical formula 4]

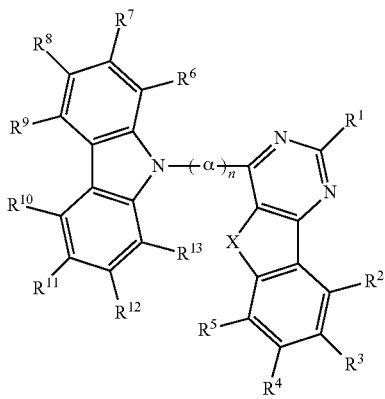

(G2)

In the general formula (G2), each of $R^1$ to $R^{13}$ independently represents any one of hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, and a substituted or unsubstituted aryl group having 6 to 13 carbon atoms. In addition, α represents a substituted or unsubstituted aromatic hydrocarbon group, and n is an integer of 1 to 4. Furthermore, X represents any one of an oxygen atom and a sulfur atom.

In particular, a light-emitting element containing, as the second organic compound, 4-{3-[3'-(9H-carbazol-9-yl)]biphenyl-3-yl}benzofuro[3,2-d]pyrimidine (abbreviation: 4mCzBPBfpm) represented by the following structural formula (100) has extremely high emission efficiency. Accordingly, 4mCzBPBfpm can be an extremely useful material for a light-emitting element in which an exciplex is used. This also applies to a light-emitting element containing, as the second organic compound, 4-{3-[3'-(9H-carbazol-9-yl)]biphenyl-3-yl}benzothieno[3,2-d]pyrimidine (abbreviation: 4mCzBPBtpm) represented by the following structural formula (200).

[Chemical formula 5]

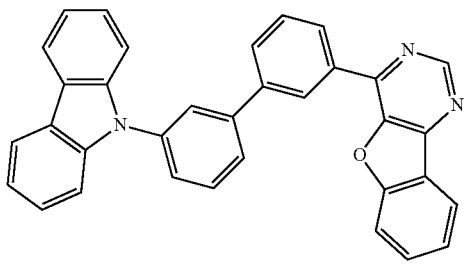

(100)

[Chemical formula 6]

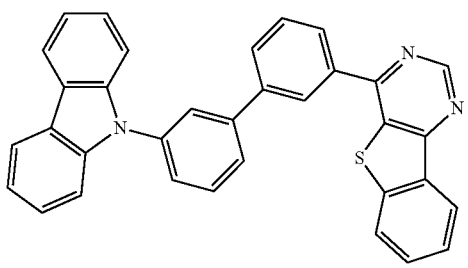

(200)

Note that when the expression "substituted or unsubstituted" is used and a substituent includes a substituent, an alkyl group having 1 to 6 carbon atoms, a phenyl group, or a biphenyl group can be used as the substituent of the substituent.

Specific examples of the above-described second organic compound can be represented by the following structural formulae (100) to (112) and structural formulae (200) to (212). Note that the second organic compound that can be used in this embodiment is not limited to the following examples.

[Chemical formulae 7]

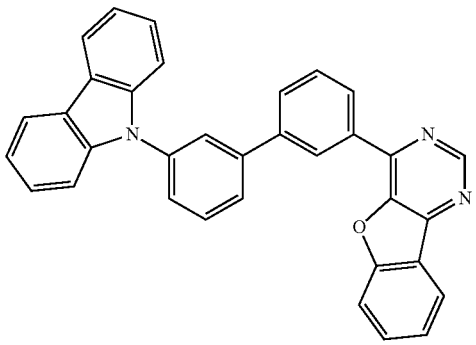

(100)

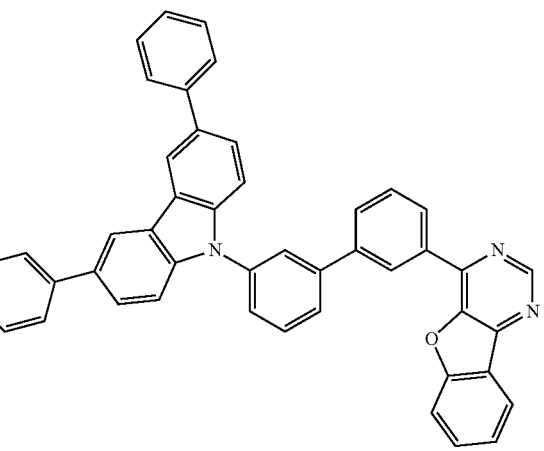

(101)

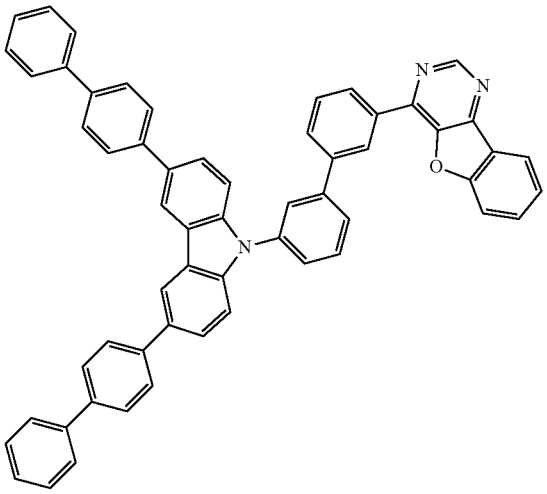

(102)

(103)
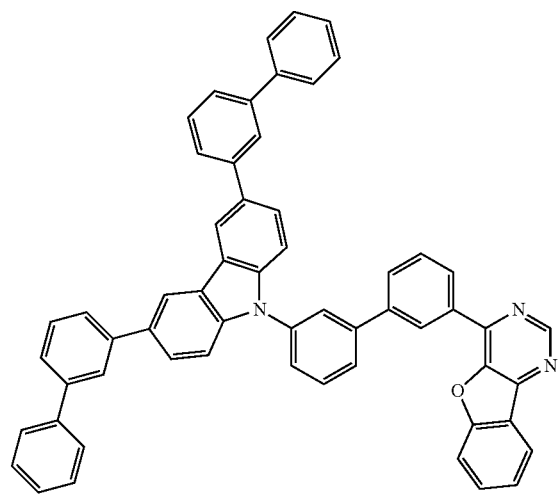
(104)
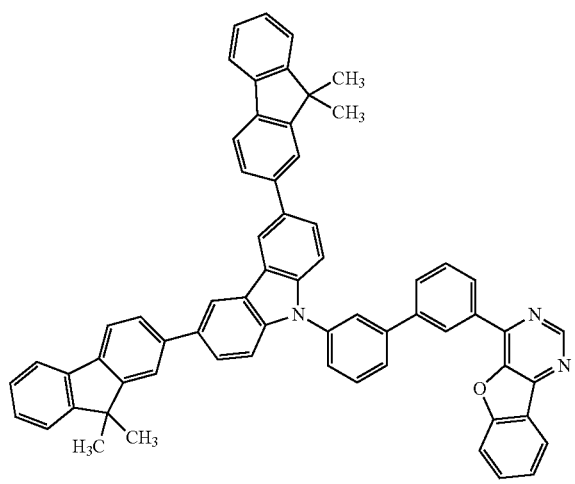
(105)
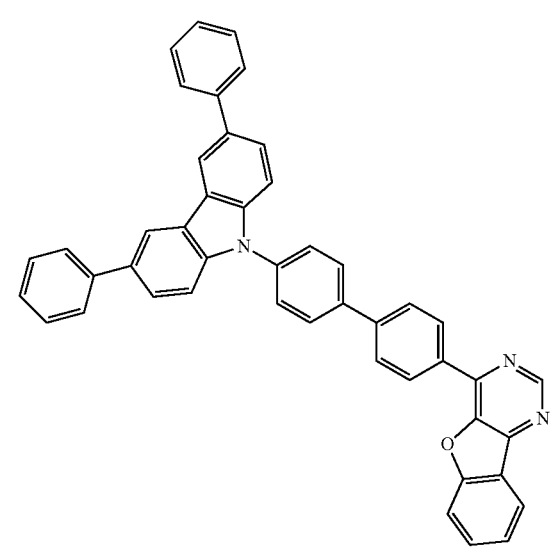
[Chemical formulae 8]
(106)
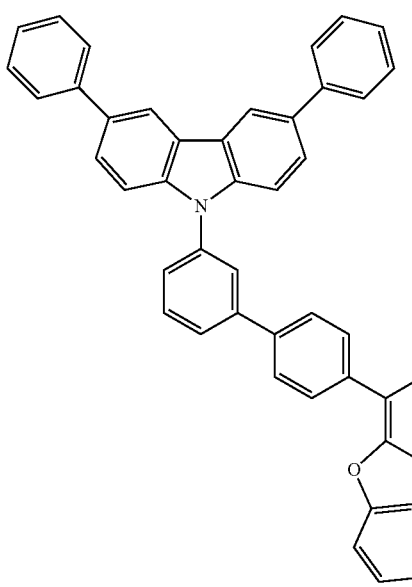
(107)
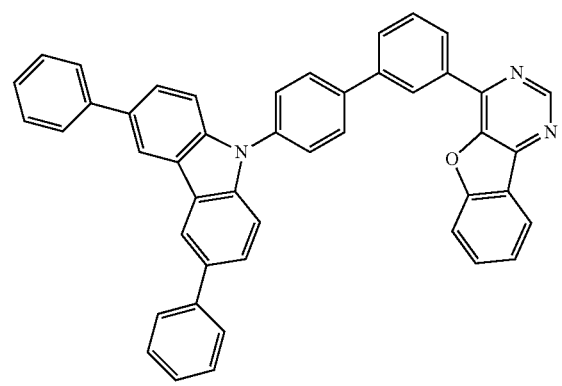
(108)
(109)
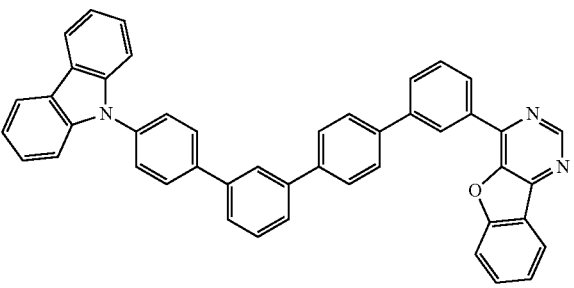

[Chemical formulae 9]
(110)
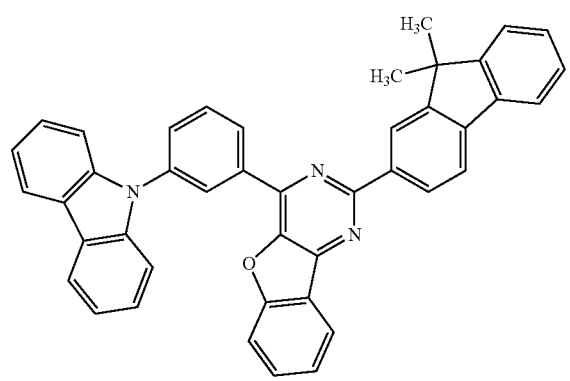
(111)
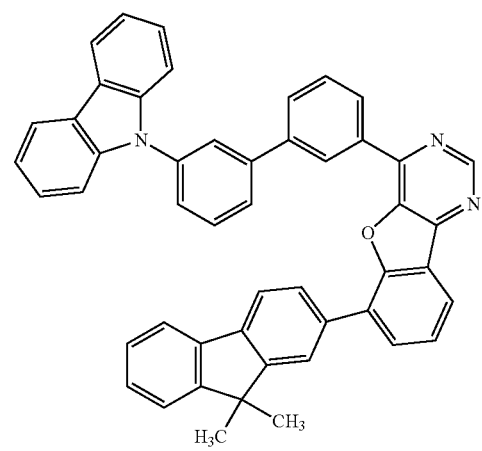
(112)
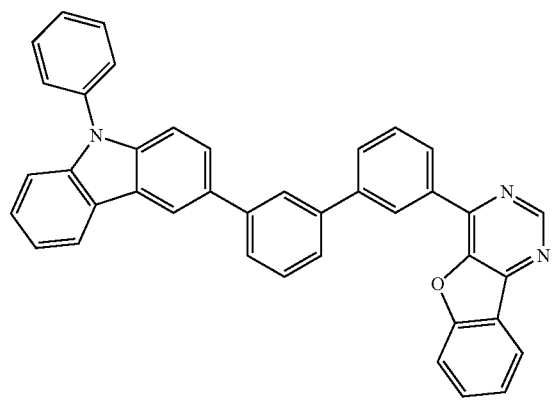
(200)
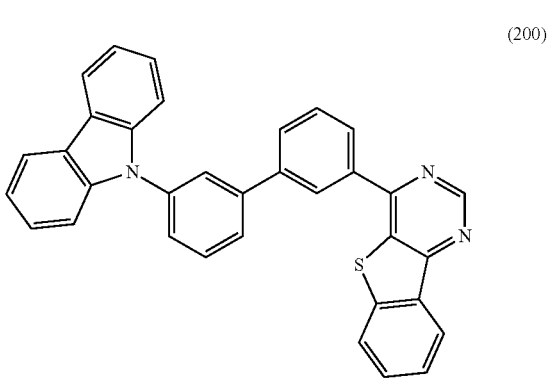
(201)
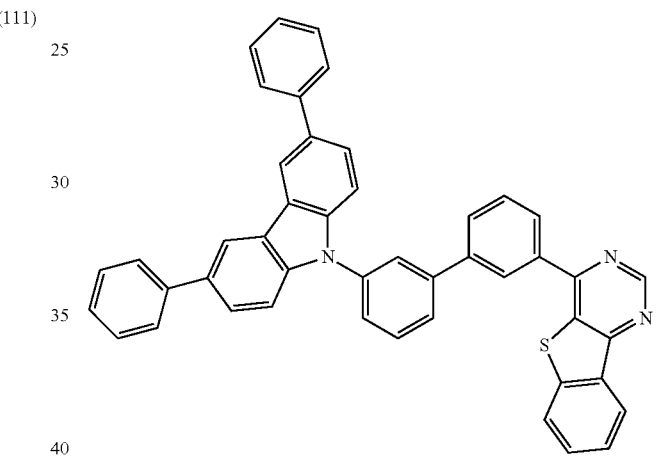
(202)
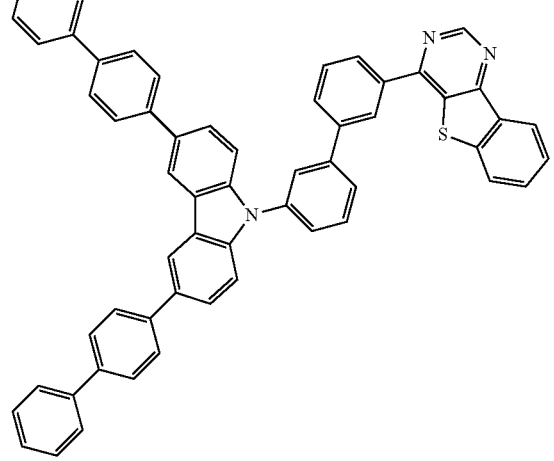

(203)
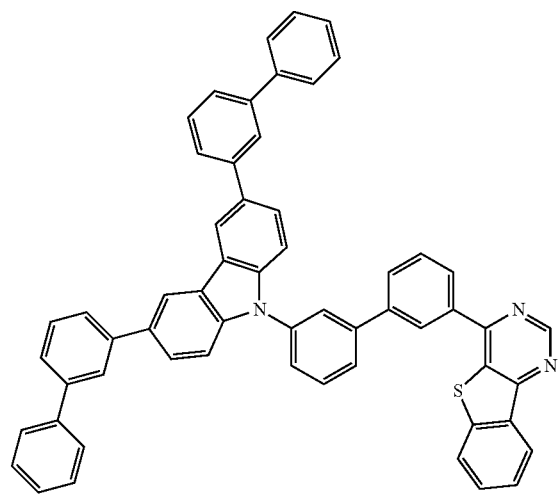
(204)
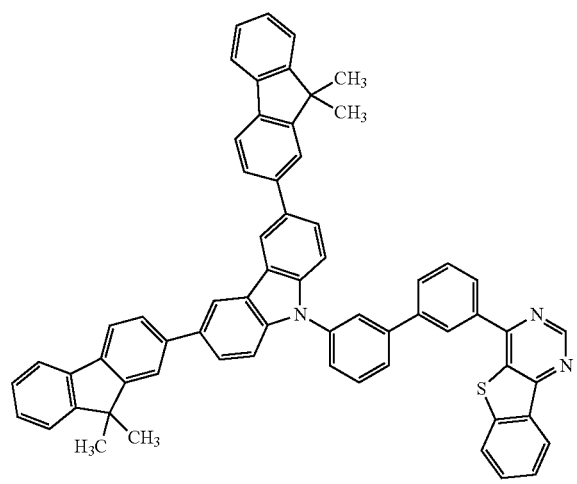
(205)
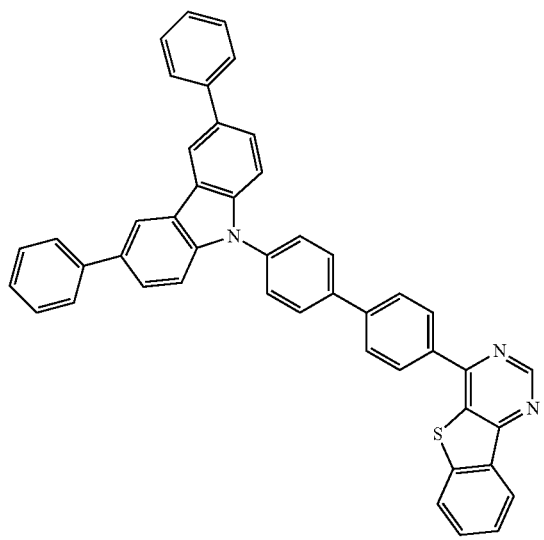
[Chemical formulae 10]
(206)
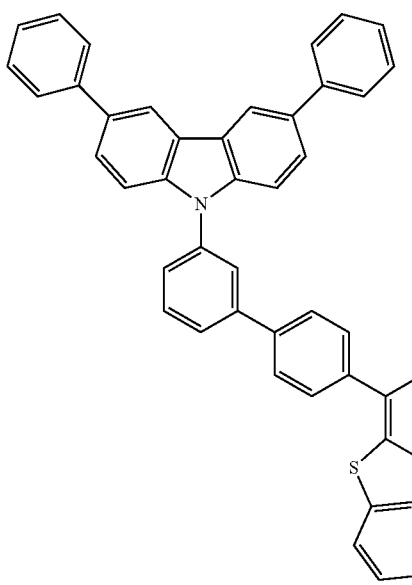
(207)
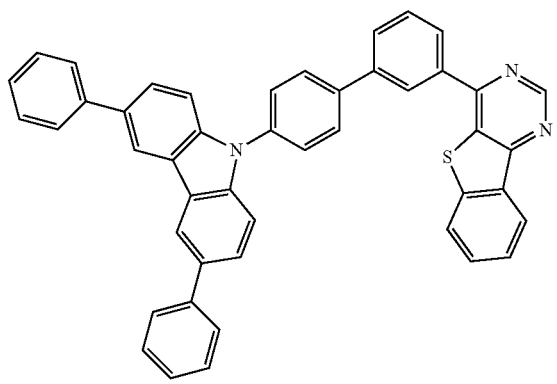
(208)
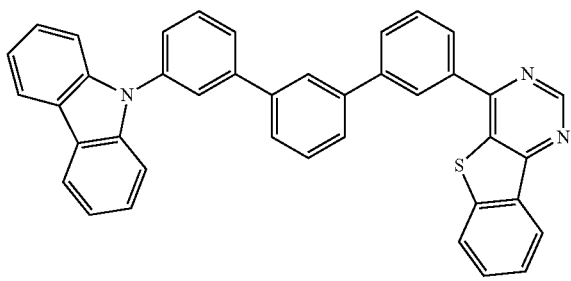
(209)
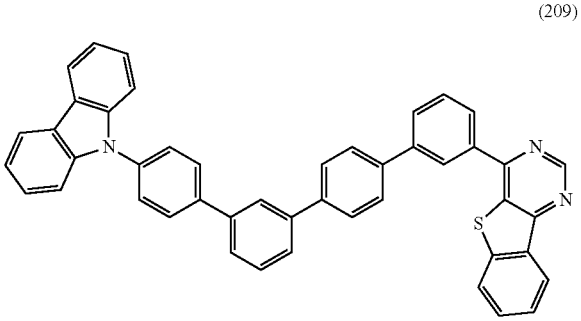

-continued

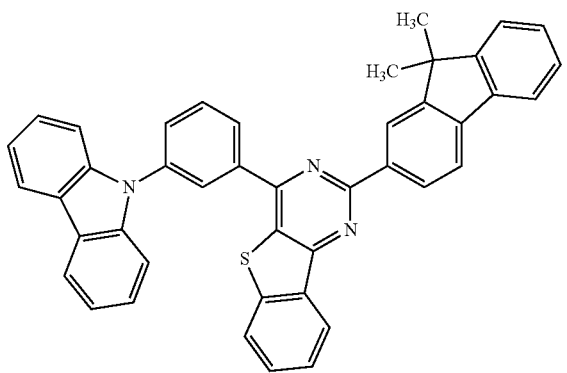
(210)

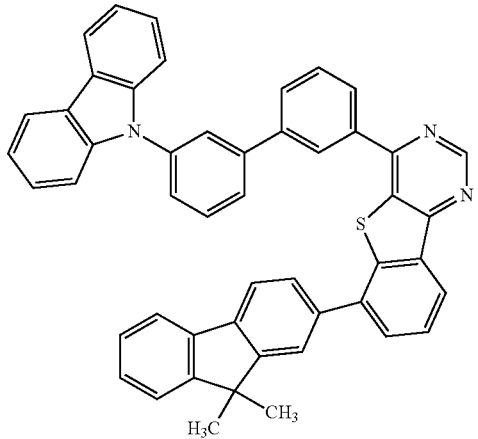
(211)

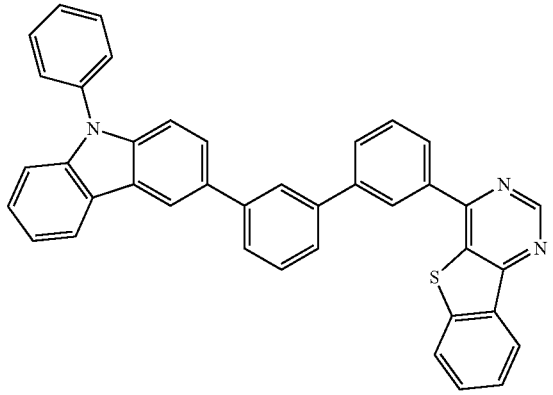
(212)

It is preferable that the triplet excitation energy of each of the first organic compound and the second organic compound (energy equivalent to a difference between a triplet excited level and a singlet excited level) be higher than the triplet excitation energy of the exciplex. This is because when the triplet excitation energy of each of the first organic compound and the second organic compound is lower than that of the exciplex, the triplet excitation energy of the exciplex is transferred, which inhibits efficient light emission.

To avoid such a disadvantage, it is preferable that the first organic compound and the second organic compound not have a naphthalene skeleton.

Note that the triplet excitation energy of an exciplex, whose singlet excited state and triplet excited state has a small energy difference, can be considered equivalent to the emission wavelength of the exciplex.

As the first organic compound having a hole-transport property, for example, a compound having a pyrrole ring, a thiophene ring, or a furan ring, a π-electron rich heteroaromatic compound such as a carbazole derivative or an indole derivative, or an aromatic amine compound is preferably used. An aromatic amine compound is particularly preferable because it can efficiently form an exciplex. Specific examples include compounds having aromatic amine skeletons, such as 2-[N-(9-phenylcarbazol-3-yl)-N-phenylamino]spiro-9,9'-bifluorene (abbreviation: PCASF), 4,4'-4"-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenylcarbazol-3-yl)-N,N'-diphenyl-benzene-1,3-diamine (abbreviation: PCA2B), N-(9,9-dimethyl-2-diphenylamino-9H-fluoren-7-yl)diphenylamine (abbreviation: DPNF), N,N',N"-triphenyl-N,N',N"-tris(9-phenylcarbazol-3-yl)benzene-1,3,5-triamine (abbreviation: PCA3B), 2-[N-(4-diphenylaminophenyl)-N-phenylamino] spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(4-diphenylaminophenyl)-N-phenylamino]biphenyl (abbreviation: DPAB), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N'-phenyl-N-(9,9-dimethyl-9H-fluoren-2-yl) amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), N,N'-bis{4-[bis(3-methylphenyl)amino]phenyl}-N,N'-diphenyl-(1,1'-biphenyl)-4,4'-diamine (abbreviation: DNTPD), 3,6-bis[N-(4-diphenylaminophenyl)-N-(1-naphthyl)amino]-9-phenylcarbazole (abbreviation: PCzTPN2), 3,6-bis[N-(9-phenylcarbazol-3-yl)-N-phenylamino]-9-phenylcarbazole (abbreviation: PCzPCA2), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 3-[N-(1-naphthyl)-N-(9-phenylcarbazol-3-yl)amino]-9-phenylcarbazole (abbreviation: PCzPCN1), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]-spiro-9,9'-bifluoren-2-amine (abbreviation: PCBASF), N-(4-biphenyl)-N-(9,9-dimethyl-9H-fluoren-2-yl)-9-phenyl-9H-carbazol-3-amine (abbreviation: PCBiF), and N-(1,1'-biphenyl-4-yl)-N-[4-(9-phenyl-9H-carbazol-3-yl)phenyl]-9,9-dimethyl-9H-fluoren-2-amine (abbreviation: PCBBiF); compounds having carbazole skeletons, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 9-phenyl-9H-3-(9-phenyl-9H-carbazol-3-yl)carbazole (abbreviation: PCCP); compounds having thiophene skeletons, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having furan skeletons, such as 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, a compound having an aromatic amine skeleton and a compound having a carbazole skeleton are preferable because these compounds are highly reliable and have high hole-transport properties to contribute to a reduction in drive voltage.

An exciplex formed by the first organic compound and the second organic compound described above can emit light with extremely high efficiency; accordingly, the light-emitting element in this embodiment can emit light with high efficiency. Although the theoretical limit of external quantum efficiency of a fluorescent light-emitting element is generally considered to be approximately 5% to 7% when it is not designed to enhance extraction efficiency, a light-emitting element having external quantum efficiency higher than the theoretical limit can be easily provided with the use of the structure of the light-emitting element in this embodiment.

As described above, because the emission wavelength of an exciplex is equivalent to a difference between a shallower HOMO level and a deeper LUMO level of the first and second organic compounds, a light-emitting element emitting light with a desired wavelength can be easily provided by selection of substances each of which has an appropriate level.

Thus, with the use of the structure in this embodiment, a highly efficient light-emitting element capable of converting a triplet excited state into light emission can be easily provided without a rare metal the supply of which is unstable. Besides, light-emitting elements with such characteristics can be provided without severe limitation on their emission wavelengths.

In this embodiment, one embodiment of the present invention has been described. Other embodiments of the present invention are described in other embodiments. Note that one embodiment of the present invention is not limited to the above examples. Although the case where a carbazole skeleton is bonded to a benzofuropyridyl group or a benzothienopyridyl group through an aromatic hydrocarbon group is described as one embodiment of the present invention, one embodiment of the present invention is not limited thereto. In one embodiment of the present invention, a structure other than the structure in which a carbazole skeleton is bonded to a benzofuropyridyl group or a benzothienopyridyl group through an aromatic hydrocarbon group may be used depending on the case and the condition. For example, in one embodiment of the present invention, a structure in which a carbazole skeleton is bonded to a benzofuropyridyl group or a benzothienopyridyl group through an aromatic hydrocarbon group is not necessarily used depending on the case and the condition.

Note that this embodiment can be implemented in appropriate combination with any of the other embodiments.

Embodiment 2

In this embodiment, a detailed example of the structure of the light-emitting element described in Embodiment 1 will be described below with reference to FIGS. 1A and 1B.

In FIG. 1A, the light-emitting element includes a first electrode 101, a second electrode 102, and a layer 103 containing an organic compound and provided between the first electrode 101 and the second electrode 102. Note that in this embodiment, the first electrode 101 functions as an anode, and the second electrode 102 functions as a cathode. In other words, when a voltage is applied between the first electrode 101 and the second electrode 102 so that the potential of the first electrode 101 is higher than that of the second electrode 102, light emission can be obtained. The layer 103 containing an organic compound includes at least a light-emitting layer 113. A hole-injection layer 111, a hole-transport layer 112, an electron-transport layer 114, and an electron-injection layer 115 which are illustrated in FIG. 1A are merely examples and not necessarily provided. A layer having any other function may also be provided.

The first electrode 101 functions as the anode and is preferably formed using any of metals, alloys, electrically conductive compounds having a high work function (specifically, a work function of 4.0 eV or more), mixtures thereof, and the like. Specific examples are indium oxide-tin oxide (ITO: indium tin oxide), indium oxide-tin oxide containing silicon or silicon oxide, indium oxide-zinc oxide, indium oxide containing tungsten oxide and zinc oxide (IWZO), and the like. Such conductive metal oxide films are usually formed by a sputtering method, but may also be formed by application of a sol-gel method or the like. In an example of the formation method, indium oxide-zinc oxide can be deposited by a sputtering method using a target in which zinc oxide is added to indium oxide at greater than or equal to 1 wt % and less than or equal to 20 wt %. Furthermore, indium oxide containing tungsten oxide and zinc oxide (IWZO) can be deposited by a sputtering method using a target in which, to indium oxide, tungsten oxide is added at greater than or equal to 0.5 wt % and less than or equal to 5 wt % and zinc oxide is added at greater than or equal to 0.1 wt % and less than or equal to 1 wt %. In addition, gold (Au), platinum (Pt), nickel (Ni), tungsten (W), chromium (Cr), molybdenum (Mo), iron (Fe), cobalt (Co), copper (Cu), palladium (Pd), a nitride of a metal material (such as titanium nitride), or the like can be used. Graphene can also be used. Note that when a composite material described later is used for a layer which is in contact with the first electrode 101 in the layer 103 containing an organic compound, an electrode material can be selected regardless of its work function.

There is no particular limitation on the stacked structure of the layer 103 containing an organic compound as long as the light-emitting layer 113 has the structure described in Embodiment 1. For example, in FIG. 1A, the layer 103 containing an organic compound can be formed by combining a hole-injection layer, a hole-transport layer, a light-emitting layer, an electron-transport layer, an electron-injection layer, a carrier-blocking layer, a charge-generation layer, and the like as appropriate. In this embodiment, the layer 103 containing an organic compound has a structure in which the hole-injection layer 111, the hole-transport layer 112, the light-emitting layer 113, the electron-transport layer 114, and the electron-injection layer 115 are stacked in this order over the first electrode 101. Materials for the layers are specifically given below.

The hole-injection layer 111 is a layer containing a substance having a high hole-injection property. Molybdenum oxide, vanadium oxide, ruthenium oxide, tungsten oxide, manganese oxide, or the like can be used. Alternatively, the hole-injection layer 111 can be formed using a phthalocyanine-based compound such as phthalocyanine (abbreviation: H₂Pc) or copper phthalocyanine (abbreviation: CuPc), an aromatic amine compound such as 4,4'-bis[N-(4-diphenylaminophenyl)-N-phenylamino]biphenyl (abbreviation: DPAB) or N,N'-bis{4-[bis(3-methylphenyl)amino]phenyl}-N,N'-diphenyl-(1,1'-biphenyl)-4,4'-diamine (abbreviation: DNTPD), a high molecular compound such as poly(3, 4-ethylenedioxythiophene)/poly(styrenesulfonic acid) (PEDOT/PSS), or the like.

Alternatively, a composite material in which a material having a hole-transport property contains a substance having an acceptor property can be used for the hole-injection layer 111. Note that the use of such a material having a hole-transport property which contains a substance having an acceptor property enables selection of a material used to form an electrode regardless of its work function. In other words, besides a material having a high work function, a material having a low work function can also be used for the first electrode 101. As the substance having an acceptor property, 7,7,8,8-tetracyano-2,3,5,6-tetrafluoroquinodimethane (abbreviation: F₄-TCNQ), chloranil, and the like can be given. In addition, transition metal oxides can be given. In addition, oxides of metals belonging to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable because it is stable in the air, has a low hygroscopic property, and is easily handled.

As the material having a hole-transport property used for the composite material, any of a variety of organic compounds such as aromatic amine compounds, carbazole derivatives, aromatic hydrocarbons, and high molecular compounds (e.g., oligomers, dendrimers, or polymers) can be used. Note that the organic compound used for the composite material is preferably an organic compound having a high hole-transport property. Specifically, a substance having a hole mobility of $10^{-6}$ cm²/Vs or higher is preferably used. Organic compounds which can be used as the material having a hole-transport property in the composite material are specifically given below.

Examples of the aromatic amine compound include N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), 1,3,5-tris[N-(4-diphenylaminophenyl)-N-phenylamino]benzene (abbreviation: DPA3B), and the like.

Specific examples of the carbazole derivative which can be used for the composite material are PCzPCA1, PCzPCA2, 3-[N-(1-naphthyl)-N-(9-phenylcarbazol-3-yl)amino]-9-phenylcarbazole (abbreviation: PCzPCN1), and the like.

In addition, examples of the carbazole derivative which can be used for the composite material include CBP, 1,3,5-tris[4-(N-carbazolyl)phenyl]benzene (abbreviation: TCPB), 9-[4-(10-phenyl-9-anthryl)phenyl]-9H-carbazole (abbreviation: CzPA), 1,4-bis[4-(N-carbazolyl)phenyl]-2,3,5,6-tetraphenylbenzene, and the like.

Examples of the aromatic hydrocarbon which can be used for the composite material include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Besides, pentacene, coronene, or the like can also be used. An aromatic hydrocarbon which has a hole mobility of $1\times10^{-6}$ cm²/Vs or higher and which has 14 to 42 carbon atoms is particularly preferable.

The aromatic hydrocarbon which can be used for the composite material may have a vinyl skeleton. Examples of the aromatic hydrocarbon having a vinyl group include 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

Moreover, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide](abbreviation: PTPDMA), or poly[N,N'-bis(4-butylphenyl)-N,N'-bis(phenyl)benzidine](abbreviation: poly-TPD) can also be used.

By providing a hole-injection layer, a high hole-injection property can be achieved to allow a light-emitting element to be driven at a low voltage.

The hole-transport layer is a layer containing a material having a hole-transport property. Examples of the material having a hole-transport property include aromatic amine compounds such as NPB, TPD, 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), BSPB, BPAFLP, and the like. The substances given here have high hole-transport properties and are mainly ones that have a hole mobility of $10^{-6}$ cm²/Vs or higher. The organic compounds given as the examples of the material having a hole-transport property in the composite material described above can also be used for the hole-transport layer. Moreover, a high molecular compound such as PVK or PVTPA can also be used. Note that the layer containing a material having a hole-transport property is not limited to a single layer, and may be a stack of two or more layers containing any of the above substances.

The light-emitting layer 113 contains the first organic compound having a hole-transport property and the second organic compound having an electron-transport property. The light-emitting layer 113 may further contain a fluorescent substance. Materials and structures of the compounds are described in Embodiment 1. By having such a structure, the light-emitting element of this embodiment has extremely high external quantum efficiency though it is a fluorescent light-emitting element which does not use a rare metal. The light-emitting element also has an advantage in that its emission wavelength can be easily adjusted and thus light in desired wavelength ranges can be easily obtained with the efficiency kept high.

The electron-transport layer 114 is a layer containing a material having an electron-transport property. For example, the electron-transport layer 114 is formed using a metal complex having a quinoline skeleton or a benzoquinoline skeleton, such as tris(8-quinolinolato)aluminum (abbreviation: Alq), tris(4-methyl-8-quinolinolato)aluminum (abbreviation: Almq₃), bis(10-hydroxybenzo[h]quinolinato)beryllium (abbreviation: BeBq₂), or bis(2-methyl-8-quinolinolato)(4-phenylphenolato)aluminum (abbreviation: BAlq), or the like. A metal complex having an oxazole-based or thiazole-based ligand, such as bis[2-(2-hydroxyphenyl)benzoxazolato]zinc (abbreviation: Zn(BOX)₂) or bis[2-(2-hydroxyphenyl)benzothiazolato]zinc (abbreviation: Zn(BTZ)₂), or the like can also be used. Other than the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances mentioned here have high electron-transport properties and are mainly ones that have an electron mobility of $10^{-6}$ cm²/Vs or higher. Note that any of the above-described second organic compounds having electron-transport properties may be used for the electron-transport layer 114.

The electron-transport layer 114 is not limited to a single layer, and may be a stack of two or more layers containing any of the above substances.

Between the electron-transport layer 114 and the light-emitting layer 113, a layer that controls transfer of electron carriers may be provided. This is a layer formed by addition of a small amount of a substance having a high electron-trapping property to the aforementioned materials having a high electron-transport property, and the layer is capable of adjusting carrier balance by suppressing transfer of electron carriers. Such a structure is very effective in preventing a problem (such as a reduction in element lifetime) caused when electrons pass through the light-emitting layer.

In addition, the electron-injection layer 115 may be provided in contact with the second electrode 102 between the electron-transport layer 114 and the second electrode 102. For the electron-injection layer 115, an alkali metal, an alkaline earth metal, or a compound thereof, such as lithium fluoride (LiF), cesium fluoride (CsF), or calcium fluoride (CaF₂), can be used. For example, a layer that is formed using a substance having an electron-transport property and contains an alkali metal, an alkaline earth metal, or a compound thereof can be used. Note that a layer that is formed using a substance having an electron-transport property and contains an alkali metal or an alkaline earth metal is preferably used as the electron-injection layer 115, in which case electron injection from the second electrode 102 is efficiently performed.

For the second electrode 102, any of metals, alloys, electrically conductive compounds, and mixtures thereof which have a low work function (specifically, a work function of 3.8 eV or less) or the like can be used. Specific examples of such a cathode material are elements belonging to Groups 1 and 2 of the periodic table, such as alkali metals (e.g., lithium (Li) and cesium (Cs)), magnesium (Mg), calcium (Ca), and strontium (Sr), alloys thereof (e.g., MgAg and AlLi), rare earth metals such as europium (Eu) and ytterbium (Yb), alloys thereof, and the like. However, when the electron-injection layer is provided between the second electrode 102 and the electron-transport layer, for the second electrode 102, any of a variety of conductive materials such as Al, Ag, ITO, or indium oxide-tin oxide containing silicon or silicon oxide can be used regardless of the work function. Films of these conductive materials can be formed by a sputtering method, an inkjet method, a spin coating method, or the like.

Any of a variety of methods can be used to form the layer 103 containing an organic compound regardless of whether it is a dry process or a wet process. For example, a vacuum evaporation method, an inkjet method, a spin coating method, or the like may be used. Different formation methods may be used for the electrodes or the layers.

In addition, the electrodes may be formed by a wet process using a sol-gel method, or by a wet process using paste of a metal material. Alternatively, the electrode may be formed by a dry process such as a sputtering method or a vacuum evaporation method.

In the light-emitting element having the above-described structure, current flows due to a potential difference between the first electrode 101 and the second electrode 102, and holes and electrons recombine in the light-emitting layer 113 which contains a substance having a high light-emitting property, so that light is emitted. In other words, a light-emitting region is formed in the light-emitting layer 113.

Light emission is extracted out through one or both of the first electrode 101 and the second electrode 102. Therefore, one or both of the first electrode 101 and the second electrode 102 are light-transmitting electrodes. In the case where only the first electrode 101 is a light-transmitting electrode, light emission is extracted through the first electrode 101. In the case where only the second electrode 102 is a light-transmitting electrode, light emission is extracted through the second electrode 102. In the case where both the first electrode 101 and the second electrode 102 are light-transmitting electrodes, light emission is extracted through the first electrode 101 and the second electrode 102.

The structure of the layers provided between the first electrode 101 and the second electrode 102 is not limited to the above-described structure. Preferably, a light-emitting region where holes and electrons recombine is positioned away from the first electrode 101 and the second electrode 102 so that quenching due to the proximity of the light-emitting region and a metal used for electrodes and carrier-injection layers can be prevented.

Further, to inhibit transfer of energy from an exciton generated in the light-emitting layer, preferably, the hole-transport layer and the electron-transport layer which are in contact with the light-emitting layer 113, particularly a carrier-transport layer in contact with a side closer to the light-emitting region in the light-emitting layer 113, are formed using a substance having a wider band gap than the exciplex included in the light-emitting layer.

Figure 1B:
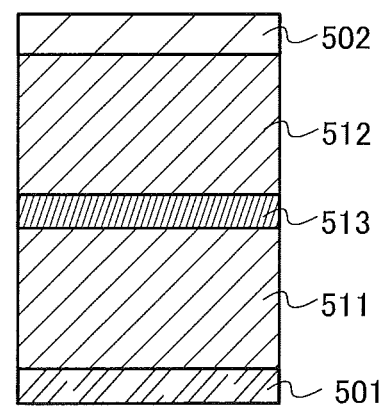

FIG. 1B shows a light-emitting element having a structure different from FIG. 1A. One embodiment of a light-emitting element in which a plurality of light-emitting units is stacked (hereinafter, also referred to as a stacked-layer element) will be described with reference to FIG. 1B. This light-emitting element is a light-emitting element including a plurality of light-emitting units between a first electrode and a second electrode. One light-emitting unit has a structure similar to that of the layer 103 containing an organic compound, which is illustrated in FIG. 1A. In other words, the light-emitting element illustrated in FIG. 1A includes a single light-emitting unit; the light-emitting element illustrated in FIG. 1B includes a plurality of light-emitting units.

In FIG. 1B, a first light-emitting unit 511 and a second light-emitting unit 512 are stacked between a first electrode 501 and a second electrode 502, and a charge-generation layer 513 is provided between the first light-emitting unit 511 and the second light-emitting unit 512. The first electrode 501 and the second electrode 502 correspond, respectively, to the first electrode 101 and the second electrode 102 illustrated in FIG. 1A, and the materials given in the description for FIG. 1A can be used. Further, the first light-emitting unit 511 and the second light-emitting unit 512 may have the same structure or different structures.

The charge-generation layer 513 contains a composite material of an organic compound and a metal oxide. As this composite material of an organic compound and a metal oxide, the composite material that can be used for the hole-injection layer illustrated in FIG. 1A can be used. As the organic compound, a variety of compounds such as an aromatic amine compound, a carbazole compound, an aromatic hydrocarbon, and a high molecular compound (such as an oligomer, a dendrimer, or a polymer) can be used. An organic compound having a hole mobility of $1 \times 10^{-6}$ cm$^2$/Vs or higher is preferably used. Note that any other substance may be used as long as the substance has a hole-transport property higher than an electron-transport property. The composite material of the organic compound and the metal oxide can achieve low-voltage driving and low-current driving because of the superior carrier-injection property and carrier-transport property. Note that in the light-emitting unit whose anode side surface is in contact with the charge-generation layer, a hole-transport layer is not necessarily provided because the charge-generation layer can also function as the hole-transport layer.

The charge-generation layer 513 may have a stacked-layer structure of a layer containing the composite material of an organic compound and a metal oxide and a layer containing another material. For example, a stacked-layer structure of a layer containing the composite material of an organic compound and a metal oxide and a layer containing a compound selected from electron-donating substances and a compound having a high electron-transport property may be formed. Moreover, a layer containing the composite material of an organic compound and a metal oxide may be stacked with a transparent conductive film.

The charge-generation layer 513 provided between the first light-emitting unit 511 and the second light-emitting unit 512 may have any structure as long as electrons can be injected to a light-emitting unit on one side and holes can be injected to a light-emitting unit on the other side when a voltage is applied between the first electrode 501 and the second electrode 502. For example, in FIG. 1B, any layer can be used as the charge-generation layer 513 as long as the layer injects electrons to the first light-emitting unit 511 and holes to the second light-emitting unit 512 when a voltage is applied such that the potential of the first electrode 501 is higher than that of the second electrode 502.

The light-emitting element having two light-emitting units is described with reference to FIG. 1B; however, the present invention can be similarly applied to a light-emitting element in which three or more light-emitting units are stacked. With a plurality of light-emitting units partitioned by the charge-generation layer between a pair of electrodes as in the light-emitting element illustrated in FIG. 1B, it is possible to provide a light-emitting element which can emit light with high luminance with the current density kept low and has a long lifetime. In addition, a low-power-consumption light-emitting device which can be driven at low voltage can be achieved.

Furthermore, when emission colors of light-emitting units are made different, light emission of a desired color can be provided from the light-emitting element as a whole. For example, in a light-emitting element having two light-emitting units, the emission colors of the first light-emitting unit may be red and green and the emission color of the second light-emitting unit may be blue, so that the light-emitting element can emit white light as the whole element.

The light-emitting element in this embodiment is preferably fabricated over a substrate of glass, plastic, or the like. As the way of stacking layers over the substrate, layers may be sequentially stacked from the first electrode 101 side or sequentially stacked from the second electrode 102 side. In a light-emitting device, although one light-emitting element may be formed over one substrate, a plurality of light-emitting elements may be formed over one substrate. With a plurality of light-emitting elements as described above formed over one substrate, a lighting device in which elements are separated or a passive matrix light-emitting device can be manufactured. Alternatively, for example, a transistor may be formed over a substrate made of glass, plastic, or the like, and a light-emitting element may be formed over an electrode that is electrically connected to the transistor. In this manner, an active matrix light-emitting device in which the driving of the light-emitting element is controlled by the transistor can be manufactured. Note that the structure of the transistor may be a top-gate structure or a bottom-gate structure, and is not limited to a particular structure. For example, a forward staggered transistor or an inverted staggered transistor may be used. Further, there is no particular limitation on the crystallinity of a semiconductor used for the transistor, and an amorphous semiconductor or a crystalline semiconductor may be used. In addition, a driver circuit formed over an element substrate may be formed with both n-type and p-type transistors or with either n-type transistors or p-type transistors.

Note that this embodiment can be combined with any of the other embodiments as appropriate.

Embodiment 3

In this embodiment, a light-emitting device including the light-emitting element described in Embodiment 1 or Embodiment 2 is described.

Figure 2A:
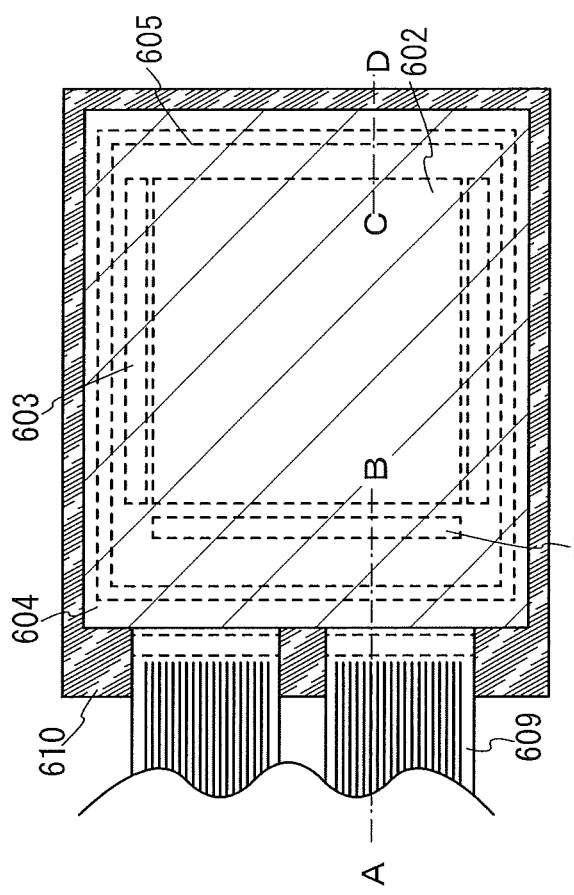
FIGS. 2A and 2B are conceptual diagrams of an active matrix light-emitting device.
Figure 2B:
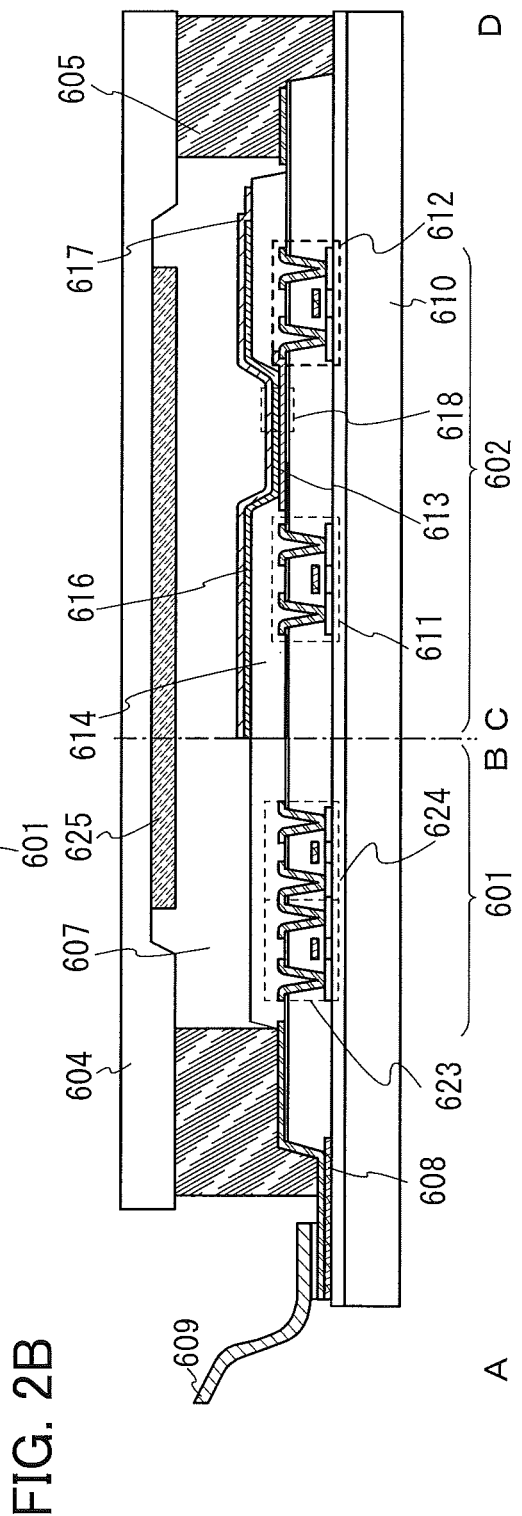

In this embodiment, a light-emitting device manufactured using the light-emitting element described in Embodiment 1 or Embodiment 2 is described with reference to FIGS. 2A and 2B. Note that FIG. 2A is a top view illustrating the light-emitting device and FIG. 2B is a cross-sectional view of FIG. 2A taken along lines A-B and C-D. This light-emitting device includes a driver circuit portion (source line driver circuit) 601, a pixel portion 602, and a driver circuit portion (gate line driver circuit) 603, which control light emission of the light-emitting element and are denoted by dotted lines. Moreover, a reference numeral 604 denotes a sealing substrate; 605, a sealing material; and 607, a space surrounded by the sealing material 605.

Note that a lead wiring 608 is a wiring for transmitting signals to be input to the source line driver circuit 601 and the gate line driver circuit 603 and for receiving a video signal, a clock signal, a start signal, a reset signal, and the like from an FPC (flexible printed circuit) 609 serving as an external input terminal. Although only the FPC is illustrated here, a printed wiring board (PWB) may be attached to the FPC. The light-emitting device in the present specification includes, in its category, not only the light-emitting device itself but also a light-emitting device provided with an FPC or a PWB.

Next, a cross-sectional structure is described with reference to FIG. 2B. The driver circuit portions and the pixel portion are formed over an element substrate 610; the source line driver circuit 601, which is a driver circuit portion, and one pixel in the pixel portion 602 are illustrated here.

In the source line driver circuit 601, a CMOS circuit is formed in which an n-channel transistor 623 and a p-channel transistor 624 are combined. Alternatively, the driver circuit may be formed with any of a variety of circuits formed using TFTs, such as a CMOS circuit, a PMOS circuit, or an NMOS circuit. Although a driver-integrated type in which the driver circuit is formed over the substrate is described in this embodiment, the present invention is not limited to this type and the driver circuit can be formed outside the substrate.

The pixel portion 602 is formed with a plurality of pixels each including a switching transistor 611, a current controlling transistor 612, and a first electrode 613 electrically connected to a drain of the current controlling transistor 612. An insulator 614 is formed to cover an end portion of the first electrode 613. Here, the insulator 614 is formed using a positive photosensitive acrylic resin film.

In order to improve the coverage, the insulator 614 is formed to have a curved surface with curvature at its upper or lower end portion. For example, in the case where positive photosensitive acrylic is used for a material of the insulator 614, only the upper end portion of the insulator 614 preferably has a curved surface with a curvature radius (greater than or equal to 0.2 μm and less than or equal to 3 μm). As the insulator 614, either a negative photosensitive resin or a positive photosensitive resin can be used.

A layer 616 containing an organic compound and a second electrode 617 are formed over the first electrode 613. As a material used for the first electrode 613 functioning as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stack including a titanium nitride film and a film containing aluminum as its main component, a stack including three layers of a titanium nitride film, a film containing aluminum as its main component, and a titanium nitride film, or the like can be used. The stacked-layer structure enables low wiring resistance, favorable ohmic contact, and a function as an anode.

In addition, the layer 616 containing an organic compound is formed by any of a variety of methods such as an evaporation method using an evaporation mask, an inkjet method, and a spin coating method. The layer 616 containing an organic compound has the structure described in Embodiment 1 or Embodiment 2. Further, for another material included in the layer 616 containing an organic compound, a low molecular compound or a high molecular compound (including an oligomer or a dendrimer) may be used.

As a material used for the second electrode 617, which is formed over the layer 616 containing an organic compound and functions as a cathode, a material having a low work function (e.g., Al, Mg, Li, Ca, or an alloy or a compound thereof, such as MgAg, MgIn, or AlLi) is preferably used. In the case where light generated in the layer 616 containing an organic compound passes through the second electrode 617, a stack including a thin metal film and a transparent conductive film (e.g., ITO, indium oxide containing zinc oxide at 2 wt % to 20 wt %, indium tin oxide containing silicon, or zinc oxide (ZnO)) is preferably used for the second electrode 617.

Note that the light-emitting element is formed with the first electrode 613, the layer 616 containing an organic compound, and the second electrode 617. The light-emitting element has the structure described in Embodiment 1 or Embodiment 2. In the light-emitting device in this embodiment, the pixel portion, which includes a plurality of light-emitting elements, may include both the light-emitting element described in Embodiment 1 or Embodiment 2 and a light-emitting element having a different structure.

Further, the sealing substrate 604 is attached to the element substrate 610 with the sealing material 605, so that the light-emitting element 618 is provided in the space 607 surrounded by the element substrate 610, the sealing substrate 604, and the sealing material 605. The space 607 is filled with filler, and may be filled with an inert gas (such as nitrogen or argon) or the sealing material 605. It is preferable that the sealing substrate be provided with a recessed portion and a desiccant 625 be provided in the recessed portion, in which case deterioration due to influence of moisture can be inhibited.

An epoxy-based resin or glass frit is preferably used for the sealing material 605. The material preferably allows as little moisture and oxygen as possible to penetrate. As the sealing substrate 604, a glass substrate, a quartz substrate, or a plastic substrate formed of fiber reinforced plastic (FRP), poly(vinyl fluoride) (PVF), polyester, acrylic, or the like can be used.

As described above, the light-emitting device which uses the light-emitting element described in Embodiment 1 or Embodiment 2 can be obtained.

The light-emitting device in this embodiment is fabricated using the light-emitting element described in Embodiment 1 or Embodiment 2 and thus can have favorable characteristics. Specifically, since the light-emitting element described in Embodiment 1 or Embodiment 2 has favorable emission efficiency, the light-emitting device can have reduced power consumption. In addition, light in desired wavelength ranges can be easily provided by the light-emitting element described in Embodiment 1 or Embodiment 2, which makes it possible to provide a versatile light-emitting device.

FIGS. 3A and 3B each illustrate an example of a light-emitting device in which full color display is achieved by formation of light-emitting elements exhibiting white light emission and with the use of coloring layers (color filters) and the like. In FIG. 3A, a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting elements, a partition 1025, a layer 1028 containing an organic compound, a second electrode 1029 of the light-emitting elements, a sealing substrate 1031, a sealing material 1032, and the like are illustrated.

In FIG. 3A, coloring layers (a red coloring layer 1034R, a green coloring layer 1034G, and a blue coloring layer 1034B) are provided on a transparent base material 1033. A black layer (a black matrix) 1035 may be additionally provided. The transparent base material 1033 provided with the coloring layers and the black layer is positioned and fixed to the substrate 1001. Note that the coloring layers and the black layer may be covered with an overcoat layer 1036. In FIG. 3A, light emitted from part of the light-emitting layer does not pass through the coloring layers, while light emitted from the other part of the light-emitting layer passes through the coloring layers. Since light which does not pass through the coloring layers is white and light which passes through any one of the coloring layers is red, blue, or green, an image can be displayed using pixels of the four colors.

FIG. 3B illustrates an example in which the coloring layers (the red coloring layer 1034R, the green coloring layer 1034G, and the blue coloring layer 1034B) are provided between the gate insulating film 1003 and the first interlayer insulating film 1020. As in the structure, the coloring layers may be provided between the substrate 1001 and the sealing substrate 1031.

Figure 4:
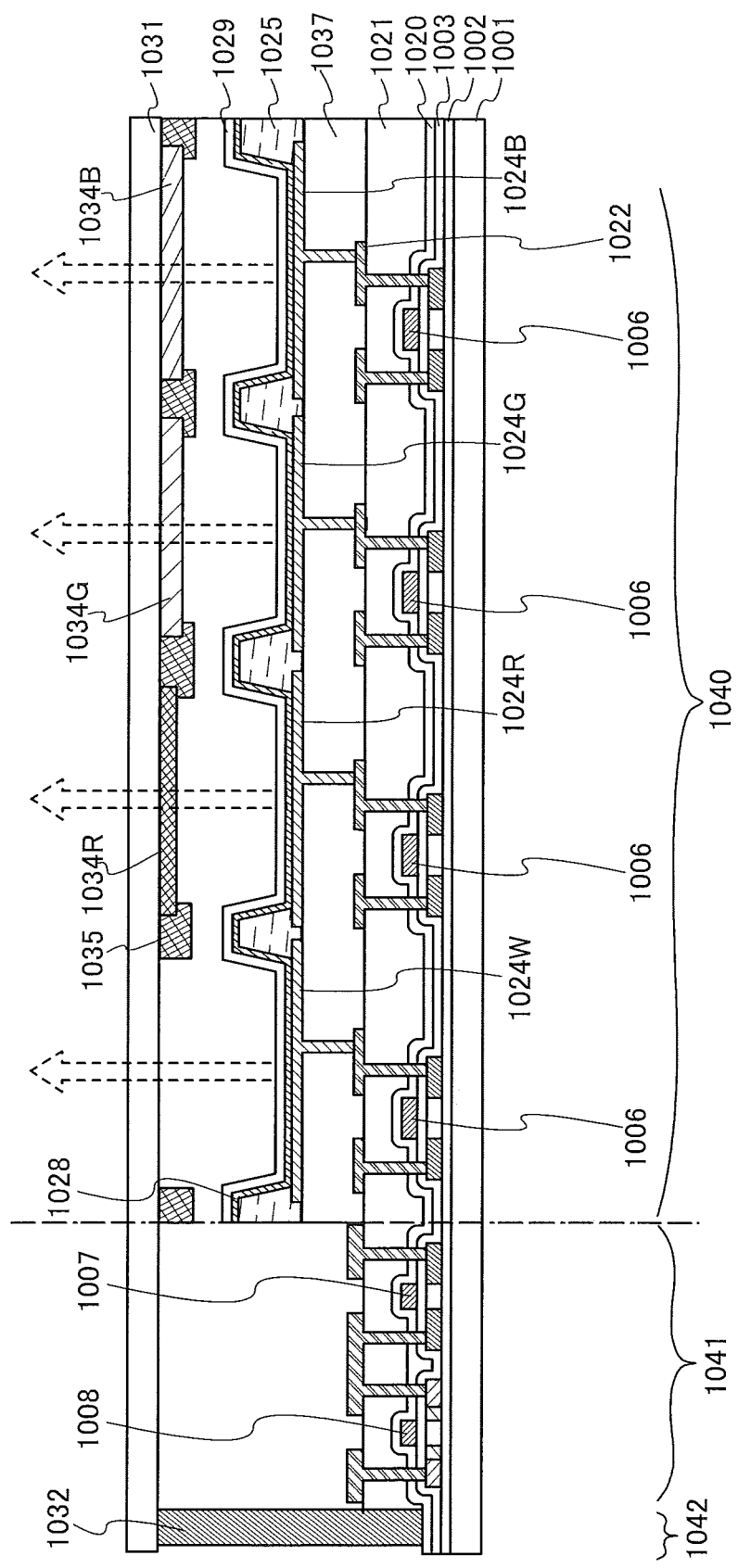
FIG. 4 is a conceptual diagram of an active matrix light-emitting device.

The above-described light-emitting device is a light-emitting device having a structure in which light is extracted from the substrate 1001 side where the transistors are formed (a bottom emission structure), but may be a light-emitting device having a structure in which light is extracted from the sealing substrate 1031 side (a top emission structure). FIG. 4 is a cross-sectional view of a light-emitting device having a top emission structure. In this case, a substrate which does not transmit light can be used as the substrate 1001. The process up to the step of forming a connection electrode which connects the TFT and the anode of the light-emitting element is performed in a manner similar to that of the light-emitting device having a bottom emission structure. Then, a third interlayer insulating film 1037 is formed to cover an electrode 1022. This insulating film may have a planarization function. The third interlayer insulating film 1037 can be formed using a material similar to that of the second interlayer insulating film, and can alternatively be formed using any of other known materials.

The first electrodes 1024W, 1024R, 1024G, and 1024B of the light-emitting elements each function as an anode here, but may function as a cathode. Further, in the case of a light-emitting device having a top emission structure as illustrated in FIG. 4, the first electrodes are preferably reflective electrodes. The layer 1028 containing an organic compound is formed to have a structure similar to the structure of the layer 103 containing an organic compound, which is described in Embodiment 1 or Embodiment 2, with which white light emission can be obtained.

In the case of a top emission structure as illustrated in FIG. 4, sealing can be performed with the sealing substrate 1031 on which the coloring layers (the red coloring layer 1034R, the green coloring layer 1034G, and the blue coloring layer 1034B) are provided. The sealing substrate 1031 may be provided with the black layer (the black matrix) 1035 which is positioned between pixels. The coloring layers (the red coloring layer 1034R, the green coloring layer 1034G, and the blue coloring layer 1034B) and the black layer (the black matrix) 1035 may be covered with an overcoat layer. Note that a light-transmitting substrate is used as the sealing substrate 1031.

Although an example in which full color display is performed using four colors of red, green, blue, and white is shown here, there is no particular limitation and full color display using three colors of red, green, and blue may be performed.

The light-emitting device in this embodiment is manufactured using the light-emitting element described in Embodiment 1 or Embodiment 2 and thus can have favorable characteristics. Specifically, since the light-emitting element described in Embodiment 1 or Embodiment 2 has favorable emission efficiency, the light-emitting device can have reduced power consumption. In addition, light in desired wavelength ranges can be easily provided by the light-emitting element described in Embodiment 1 or Embodiment 2, which makes it possible to provide a versatile light-emitting device.

Figure 5A:
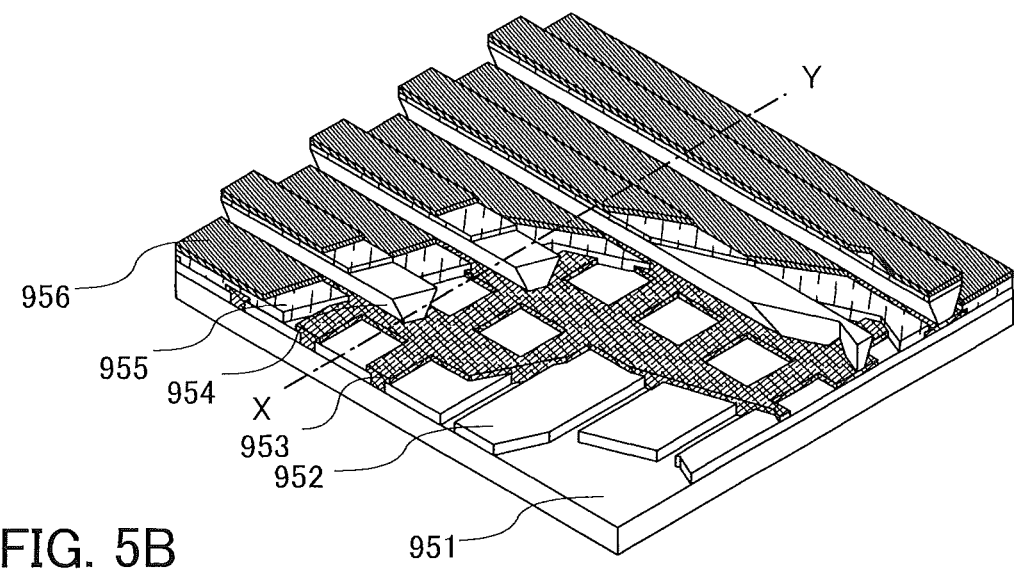
FIGS. 5A and 5B are conceptual diagrams of a passive matrix light-emitting device.
Figure 5B:
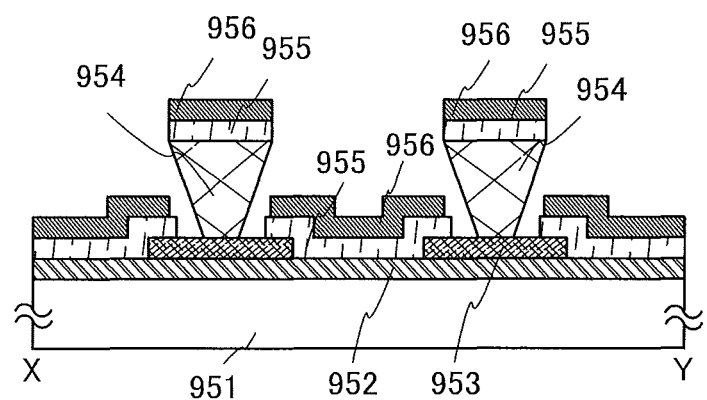

An active matrix light-emitting device is described above, whereas a passive matrix light-emitting device is described below. FIGS. 5A and 5B illustrate a passive matrix light-emitting device manufactured using the present invention. FIG. 5A is a perspective view of the light-emitting device, and FIG. 5B is a cross-sectional view of FIG. 5A taken along line X-Y. In FIGS. 5A and 5B, a layer 955 containing an organic compound is provided between an electrode 952 and an electrode 956 over a substrate 951. An end portion of the electrode 952 is covered with an insulating layer 953. A partition layer 954 is provided over the insulating layer 953. Sidewalls of the partition layer 954 slope such that the distance between both sidewalls is gradually narrowed toward the surface of the substrate. In other words, a cross section taken along the direction of the short side of the partition layer 954 is trapezoidal, and the lower side (a side which is in the same direction as a plane direction of the insulating layer 953 and in contact with the insulating layer 953) is shorter than the upper side (a side which is in the same direction as the plane direction of the insulating layer 953 and not in contact with the insulating layer 953). The partition layer 954 thus provided can prevent defects in the light-emitting element due to static electricity or the like. Furthermore, the passive matrix light-emitting device can also have lower power consumption by including the light-emitting element described in Embodiment 1 or Embodiment 2, which has favorable emission efficiency. In addition, light in desired wavelength ranges can be easily provided by the light-emitting element described in Embodiment 1 or Embodiment 2, which makes it possible to provide a versatile light-emitting device.

Since many minute light-emitting elements arranged in a matrix in any of the light-emitting devices described above can each be controlled, the light-emitting devices can be suitably used as display devices for displaying images.

This embodiment can be freely combined with any of other embodiments.

Embodiment 4

Figure 6A:
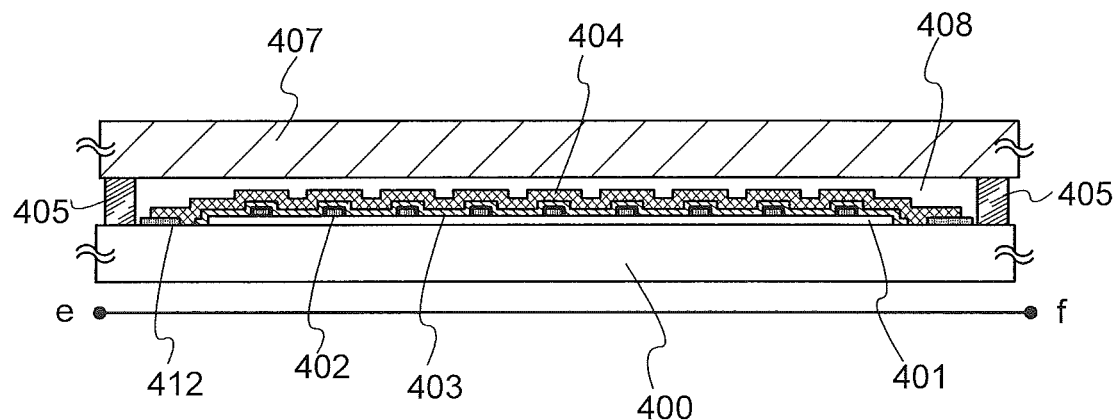
FIGS. 6A and 6B are conceptual diagrams of a lighting device.
Figure 6B:
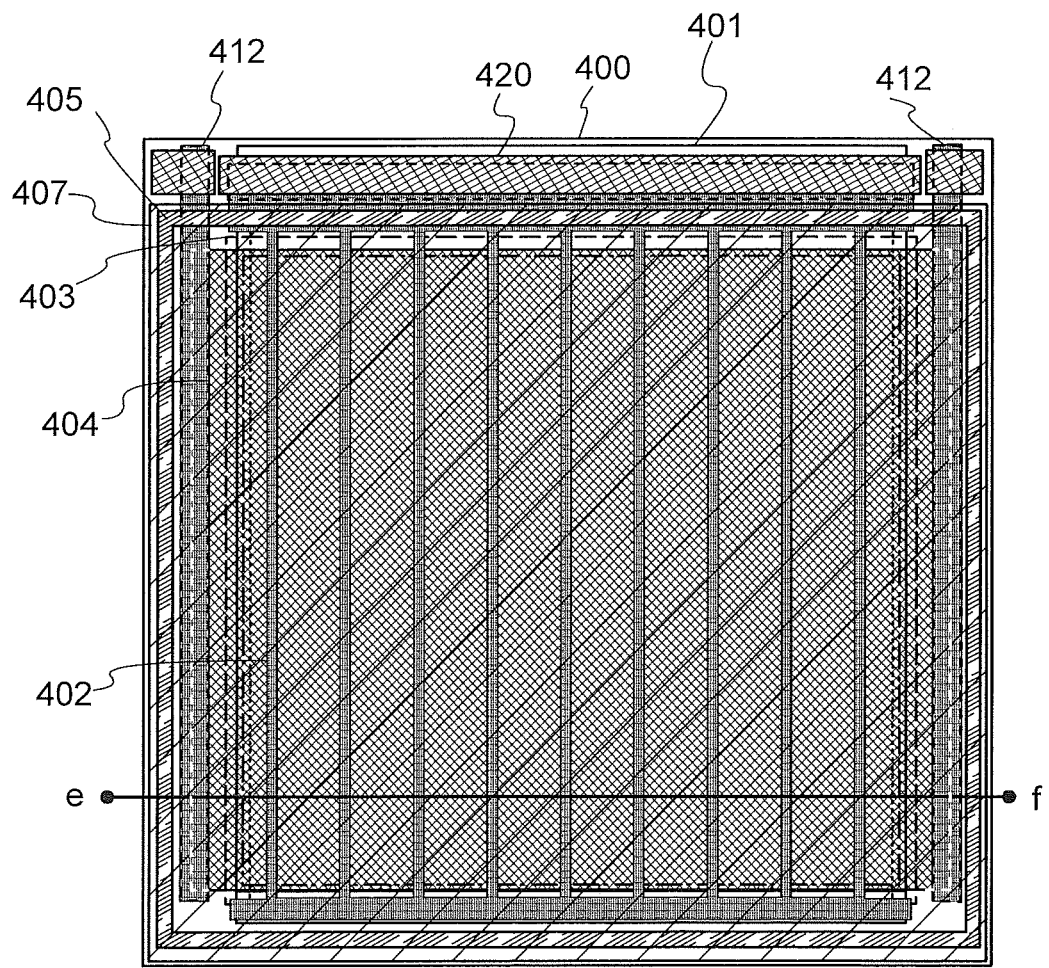

In this embodiment, an example in which the light-emitting element described in Embodiment 1 or Embodiment 2 is used for a lighting device is described with reference to FIGS. 6A and 6B. FIG. 6B is a top view of the lighting device, and FIG. 6A is a cross-sectional view of FIG. 6B taken along line e-f.

In the lighting device in this embodiment, a first electrode 401 is formed over a substrate 400 which is a support and has a light-transmitting property. The first electrode 401 corresponds to the first electrode 101 in Embodiment 2. When light is extracted through the first electrode 401 side, the first electrode 401 is formed using a material having a light-transmitting property.

A pad 412 for applying voltage to a second electrode 404 is provided over the substrate 400.

A layer 403 containing an organic compound is formed over the first electrode 401. The structure of the layer 403 containing an organic compound corresponds to, for example, the structure of the layer 103 containing an organic compound in Embodiment 2, or the structure in which the light-emitting units 511 and 512 and the charge-generation layer 513 are combined. For these structures, the description in Embodiment 2 can be referred to. A black layer (black matrix) 402 is also formed.

The second electrode 404 is formed to cover the layer 403 containing an organic compound. The second electrode 404 corresponds to the second electrode 102 in Embodiment 2. The second electrode 404 is formed using a material having high reflectance when light is extracted through the first electrode 401 side. The second electrode 404 is connected to the pad 412, whereby voltage is applied thereto.

As described above, the lighting device described in this embodiment includes the light-emitting element including the first electrode 401, the layer 403 containing an organic compound, and the second electrode 404. Since the light-emitting element is inexpensive and excellent in durability, the lighting device in this embodiment can have high emission efficiency.

The substrate 400 provided with the light-emitting element having the above structure is attached to a sealing substrate 407 with a sealing material 405, whereby the lighting-emitting element is sealed. A space 408 is preferably in a reduced pressure.

When parts of the pad 412 and the first electrode 401 are extended to the outside of the sealing material 405, the extended parts can serve as external input terminals. An IC chip 420 mounted with a converter or the like may be provided over the external input terminals.

As described above, since the lighting device described in this embodiment includes the light-emitting element described in Embodiment 1 or Embodiment 2, the lighting device can have high emission efficiency.

Embodiment 5

In this embodiment, examples of electronic devices each including the light-emitting element described in Embodiment 1 or Embodiment 2 are described. The light-emitting element described in Embodiment 1 or Embodiment 2 has high emission efficiency and accordingly, the electronic devices in this embodiment each of which includes the light-emitting element can have low power consumption.

Examples of the electronic devices to which the above light-emitting element is applied include television devices (also referred to as TV or television receivers), monitors for computers and the like, cameras such as digital cameras and digital video cameras, digital photo frames, mobile phones (also referred to as cell phones or mobile phone devices), portable game machines, portable information terminals, audio playback devices, large game machines such as pachinko machines, and the like. Specific examples of these electronic devices are described below.

Figure 7A:
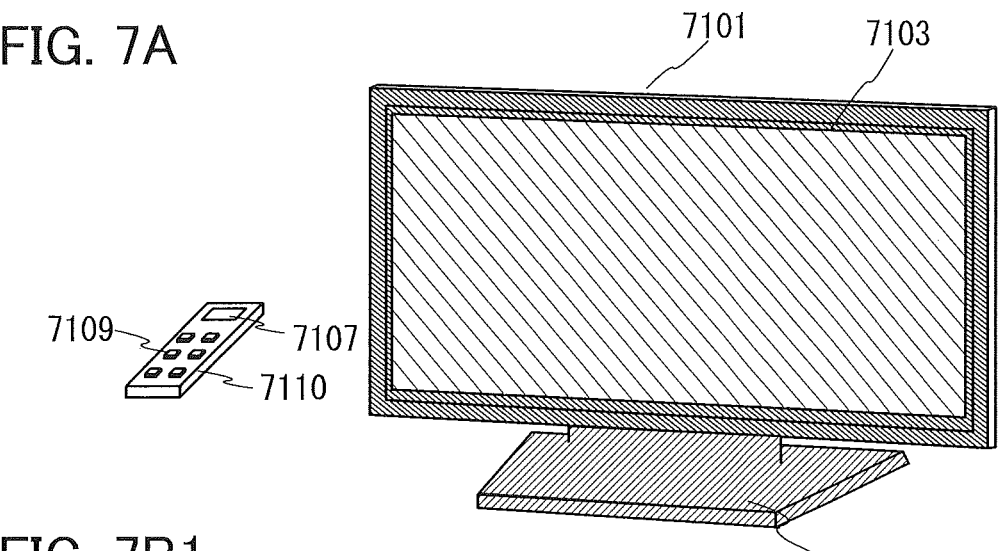
Figure 7A:
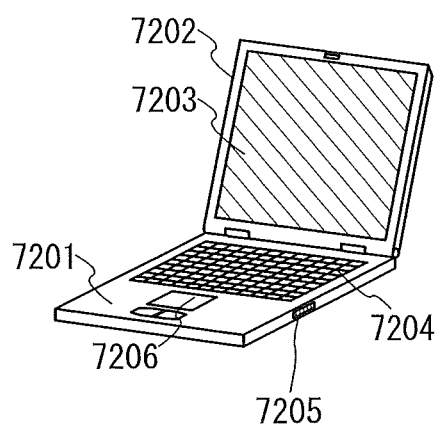
Figure 7A:
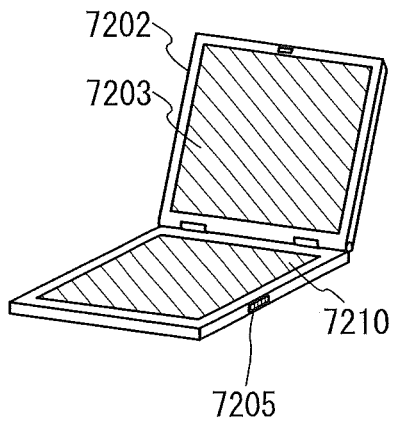

FIG. 7A illustrates an example of a television device. In the television device, a display portion 7103 is incorporated in a housing 7101. Here, the housing 7101 is supported by a stand 7105. Images can be displayed on the display portion 7103, and in the display portion 7103, the light-emitting elements described in Embodiment 1 or Embodiment 2 are arranged in a matrix. The light-emitting elements can have high emission efficiency. Therefore, the television device including the display portion 7103 which is formed using the light-emitting elements can have low power consumption.

The television device can be operated with an operation switch of the housing 7101 or a separate remote controller 7110. With operation keys 7109 of the remote controller 7110, channels and volume can be controlled and images displayed on the display portion 7103 can be controlled. Further, the remote controller 7110 may be provided with a display portion 7107 for displaying data output from the remote controller 7110.

Note that the television device is provided with a receiver, a modem, and the like. With the use of the receiver, general television broadcasting can be received. Moreover, when the television device is connected to a communication network with or without wires via the modem, one-way (from a sender to a receiver) or two-way (between a sender and a receiver or between receivers) information communication can be performed.

FIG. 7B1 illustrates a computer, which includes a main body 7201, a housing 7202, a display portion 7203, a keyboard 7204, an external connection port 7205, a pointing device 7206, and the like. Note that this computer is manufactured using light-emitting elements arranged in a matrix in the display portion 7203, which are the same as that described in Embodiment 1 or Embodiment 2. The computer illustrated in FIG. 7B1 may have a structure illustrated in FIG. 7B2. The computer illustrated in FIG. 7B2 is provided with a second display portion 7210 instead of the keyboard 7204 and the pointing device 7206. The second display portion 7210 is a touchscreen, and input can be performed by operation of display for input on the second display portion 7210 with a finger or a dedicated pen. The second display portion 7210 can also display images other than the display for input. The display portion 7203 may also be a touchscreen. Connecting the two screens with a hinge can prevent troubles; for example, the screens can be prevented from being cracked or broken while the computer is being stored or carried. Note that this computer is manufactured using light-emitting elements arranged in a matrix in the display portion 7203, which are the same as that described in Embodiment 1 or Embodiment 2. Therefore, this computer having the display portion 7203 which is formed using the light-emitting elements consumes less power.

Figure 7C:
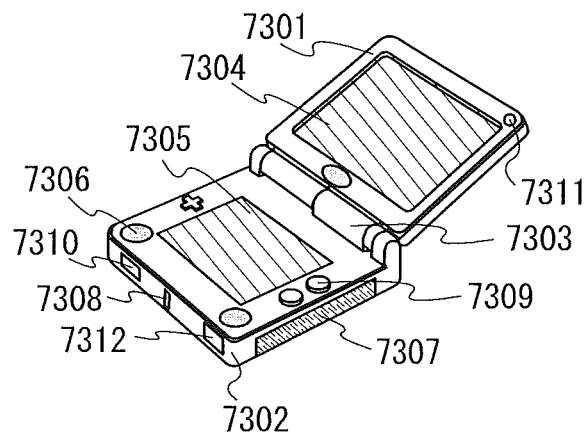

FIG. 7C illustrates a portable game machine, which includes two housings, a housing 7301 and a housing 7302, which are connected with a joint portion 7303 so that the portable game machine can be opened or folded. The housing 7301 incorporates a display portion 7304 including light-emitting elements each of which is described in Embodiment 1 or Embodiment 2 and which are arranged in a matrix, and the housing 7302 incorporates a display portion 7305. In addition, the portable game machine illustrated in FIG. 7C includes a speaker portion 7306, a recording medium insertion portion 7307, an LED lamp 7308, input units (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), and a microphone 7312), and the like. Needless to say, the structure of the portable game machine is not limited to the above as long as the display portion including the light-emitting elements each of which is described in Embodiment 1 or Embodiment 2 and which are arranged in a matrix is used as either the display portion 7304 or the display portion 7305, or both, and the structure can include other accessories as appropriate. The portable game machine illustrated in FIG. 7C has a function of reading out a program or data stored in a storage medium to display it on the display portion, and a function of sharing information with another portable game machine by wireless communication. The portable game machine illustrated in FIG. 7C can have a variety of functions without limitation to the above. The portable game machine having the display portion 7304 can have low power consumption because the light-emitting elements described in Embodiment 1 or Embodiment 2 are used in the display portion 7304.

Figure 7D:
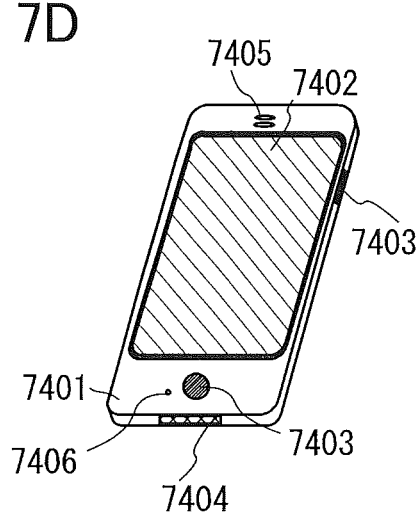

FIG. 7D illustrates an example of a mobile phone. The mobile phone is provided with a display portion 7402 incorporated in a housing 7401, operation buttons 7403, an external connection port 7404, a speaker 7405, a microphone 7406, and the like. Note that the mobile phone has the display portion 7402 including the light-emitting elements each of which is described in Embodiment 1 or Embodiment 2 and which are arranged in a matrix. Accordingly, the mobile phone can have low power consumption.

When the display portion 7402 of the mobile phone illustrated in FIG. 7D is touched with a finger or the like, data can be input into the mobile phone. In this case, operations such as making a call and composing e-mail can be performed by touch on the display portion 7402 with a finger or the like.

There are mainly three screen modes of the display portion 7402. The first mode is a display mode mainly for displaying images. The second mode is an input mode mainly for inputting data such as characters. The third mode is a display-and-input mode in which two modes of the display mode and the input mode are combined.

For example, in the case of making a call or composing e-mail, a character input mode mainly for inputting characters is selected for the display portion 7402 so that characters displayed on a screen can be input. In this case, it is preferable to display a keyboard or number buttons on almost the entire screen of the display portion 7402.

When a sensing device which includes a sensor for sensing inclination, such as a gyroscope or an acceleration sensor, is provided inside the mobile phone, the direction of the mobile phone (whether the mobile phone is placed horizontally or vertically for a landscape mode or a portrait mode) is determined so that display on the screen of the display portion 7402 can be automatically switched.

The screen modes are switched by touching the display portion 7402 or operating the operation buttons 7403 of the housing 7401. Alternatively, the screen modes can be switched depending on the kinds of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed within a specified period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, whereby personal authentication can be performed. Further, by providing a backlight or a sensing light source which emits near-infrared light in the display portion, an image of a finger vein, a palm vein, or the like can be taken.

Note that the structure described in this embodiment can be combined with any of the structures described in Embodiments 1 and 2 as appropriate.

As described above, the application range of the light-emitting device including the light-emitting element described in Embodiment 1 or Embodiment 2 is extremely wide; therefore, the light-emitting device can be applied to electronic devices of a variety of fields. By using the light-emitting element described in Embodiment 1 or Embodiment 2, an electronic device having low power consumption can be obtained.

Figure 8:
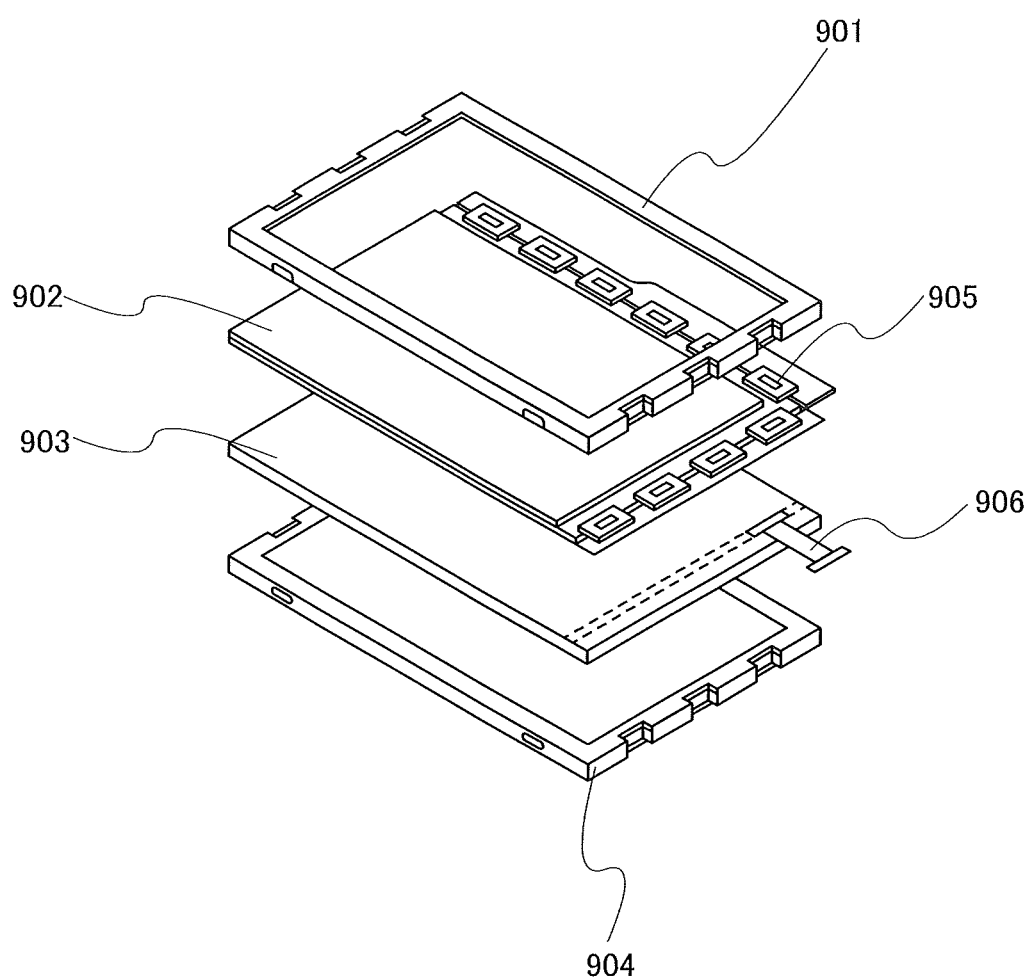
FIG. 8 illustrates an electronic device.

FIG. 8 illustrates an example of a liquid crystal display device using the light-emitting element described in Embodiment 1 or Embodiment 2 for a backlight. The liquid crystal display device shown in FIG. 8 includes a housing 901, a liquid crystal layer 902, a backlight unit 903, and a housing 904. The liquid crystal layer 902 is connected to a driver IC 905. The light-emitting element described in Embodiment 1 or Embodiment 2 is used for the backlight unit 903, to which current is supplied through a terminal 906.

The light-emitting element described in Embodiment 1 or Embodiment 2 is used for the backlight of the liquid crystal display device; thus, the backlight can have reduced power consumption. In addition, the use of the light-emitting element described in Embodiment 1 or Embodiment 2 enables manufacture of a planar-emission lighting device and further a larger-area planar-emission lighting device; therefore, the backlight can be a larger-area backlight, and the liquid crystal display device can also be a larger-area device. Furthermore, the light-emitting device using the light-emitting element described in Embodiment 1 or Embodiment 2 can be thinner than a conventional one; accordingly, the display device can also be thinner.

Figure 9A:
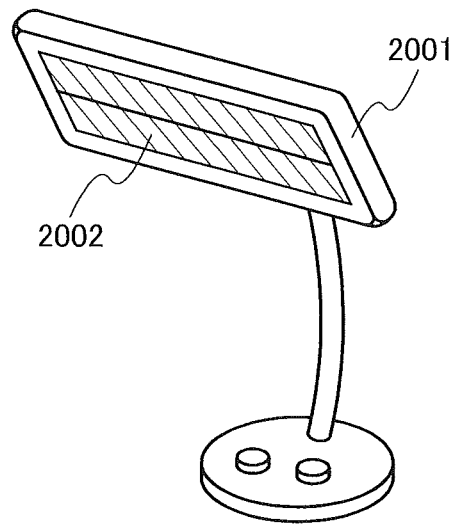
FIGS. 9A and 9B illustrate lighting devices.

FIG. 9A illustrates an example in which the light-emitting element described in Embodiment 1 or Embodiment 2 is used for a table lamp which is a lighting device. The table lamp illustrated in FIG. 9A includes a housing 2001 and a light source 2002, and the lighting device described in Embodiment 4 is used for the light source 2002.

Figure 10:
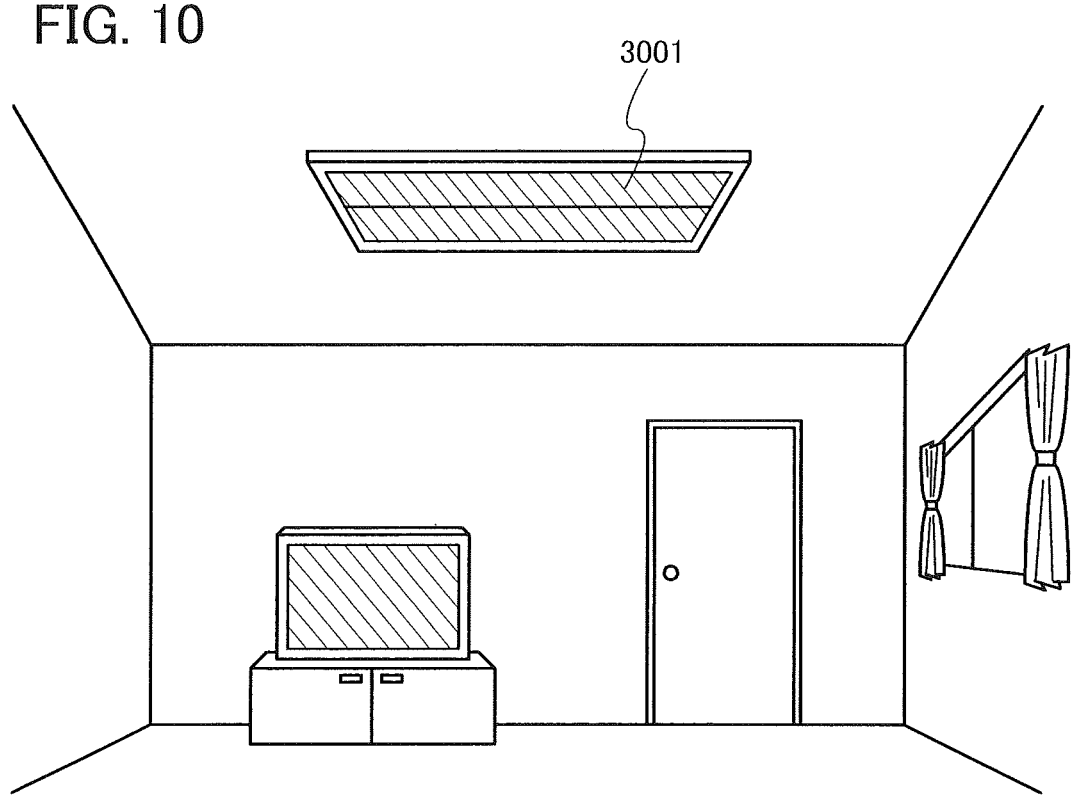
FIG. 10 illustrates a lighting device.

FIG. 10 illustrates an example in which the light-emitting element described in Embodiment 1 or Embodiment 2 is used for an indoor lighting device 3001. Since the light-emitting element described in Embodiment 1 or Embodiment 2 has low power consumption, a lighting device having low power consumption can be obtained. Further, since the light-emitting element described in Embodiment 1 or Embodiment 2 can have a large area, the light-emitting element can be used for a large-area lighting device. Furthermore, since the light-emitting element described in Embodiment 1 or Embodiment 2 is thin, the light-emitting element can be used for a lighting device having a reduced thickness.

Figure 11:
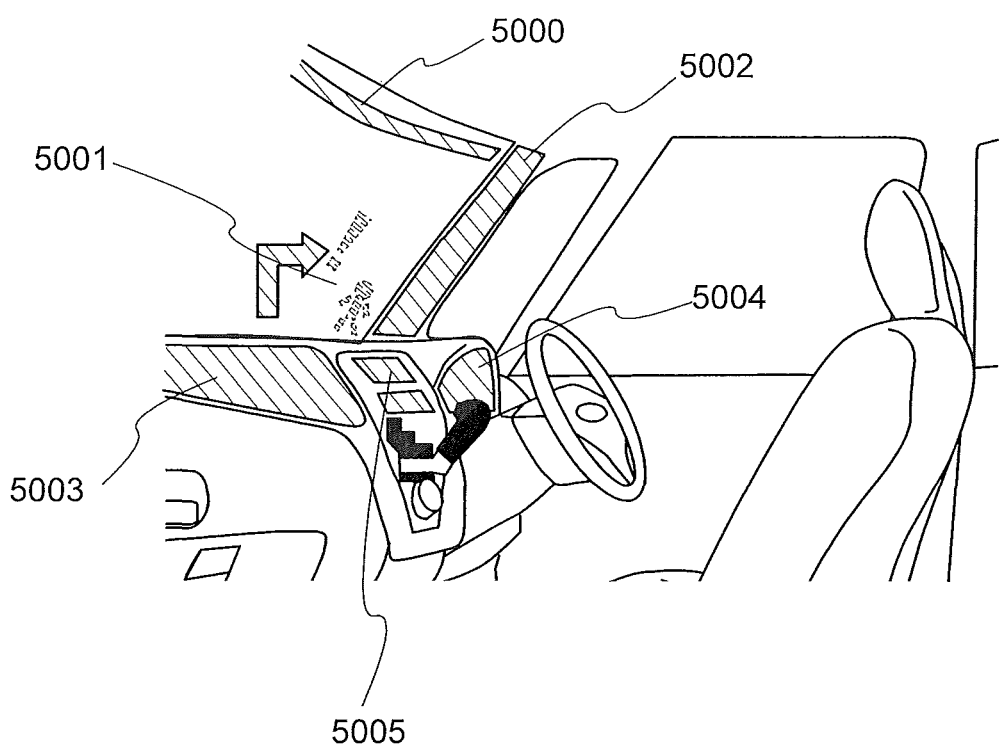
FIG. 11 illustrates in-vehicle display devices and lighting devices.

The light-emitting element described in Embodiment 1 or Embodiment 2 can also be used for an automobile windshield or an automobile dashboard. FIG. 11 illustrates one mode in which the light-emitting element described in Embodiment 1 or Embodiment 2 is used for an automobile windshield and an automobile dashboard. Display regions 5000 to 5005 each include the light-emitting element described in Embodiment 1 or Embodiment 2.

The display region 5000 and the display region 5001 are display devices which are provided in the automobile windshield and in which the light-emitting element described in Embodiment 1 or Embodiment 2 is incorporated. The light-emitting element described in Embodiment 1 or Embodiment 2 can be formed into what is called a see-through display device, through which the opposite side can be seen, by including a first electrode and a second electrode formed of electrodes having light-transmitting properties. Such see-through display devices can be provided even in the automobile windshield, without hindering the vision. Note that in the case where a transistor for driving or the like is provided, a transistor having a light-transmitting property, such as an organic transistor using an organic semiconductor material or a transistor using an oxide semiconductor, is preferably used.

The display region 5002 is a display device provided in a pillar portion in which the light-emitting elements described in Embodiment 1 or Embodiment 2 are incorporated. The display region 5002 can compensate for the view hindered by the pillar portion by showing an image taken by an imaging unit provided in the car body. Similarly, the display region 5003 provided in the dashboard can compensate for the view hindered by the car body by showing an image taken by an imaging unit provided in the outside of the car body, which leads to elimination of blind areas and enhancement of safety. Showing an image so as to compensate for the area which a driver cannot see makes it possible for the driver to confirm safety easily and comfortably.

The display region 5004 and the display region 5005 can provide a variety of kinds of information such as navigation data, a speedometer, a tachometer, a mileage, a fuel meter, a gearshift indicator, and air-condition setting. The content or layout of the display can be changed freely by a user as appropriate. Further, such information can also be shown by the display regions 5000 to 5003. Note that the display regions 5000 to 5005 can also be used as lighting devices.

The light-emitting element described in Embodiment 1 or Embodiment 2 can have low power consumption.

For that reason, load on a battery is small even when a number of large screens such as the display regions 5000 to 5005 are provided, which provides comfortable use. For that reason, the light-emitting device and the lighting device each of which includes the light-emitting element described in Embodiment 1 or Embodiment 2 can be suitably used as an in-vehicle light-emitting device and an in-vehicle lighting device.

Figure 12A:
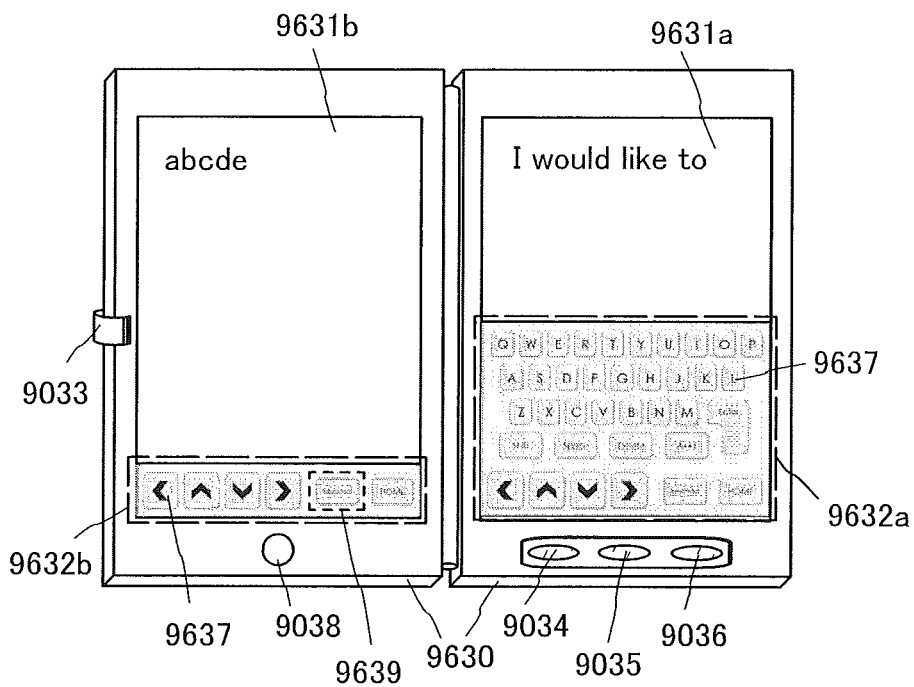
FIGS. 12A to 12C illustrate an electronic device.
Figure 12B:
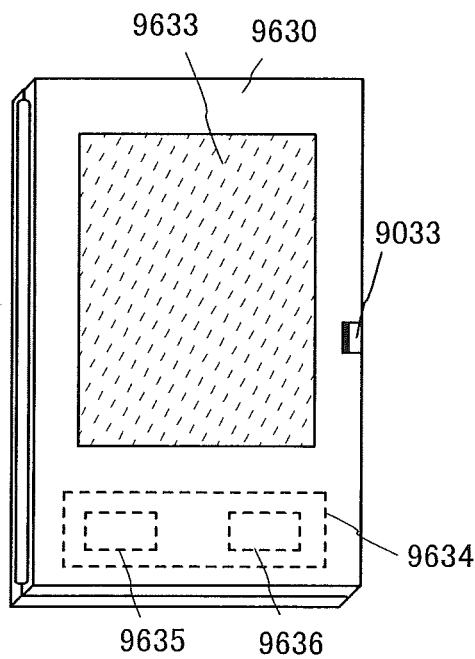

FIGS. 12A and 12B illustrate an example of a foldable tablet terminal. The tablet terminal is opened in FIG. 12A. The tablet terminal includes a housing 9630, a display portion 9631a, a display portion 9631b, a display mode switch 9034, a power switch 9035, a power saver switch 9036, a clasp 9033, and an operation switch 9038. Note that in the tablet terminal, one or both of the display portion 9631a and the display portion 9631b is/are formed using a light-emitting device which includes the light-emitting element described in Embodiment 1 or Embodiment 2.

Part of the display portion 9631a can be a touchscreen region 9632a and data can be input when a displayed operation key 9637 is touched. Although half of the display portion 9631a has only a display function and the other half has a touchscreen function, one embodiment of the present invention is not limited to the structure. The whole display portion 9631a may have a touchscreen function. For example, a keyboard can be displayed on the entire region of the display portion 9631a so that the display portion 9631a is used as a touchscreen, and the display portion 9631b can be used as a display screen.

Like the display portion 9631a, part of the display portion 9631b can be a touchscreen region 9632b. A switching button 9639 for showing/hiding a keyboard of the touchscreen is touched with a finger, a stylus, or the like, so that keyboard buttons can be displayed on the display portion 9631b.

Touch input can be performed in the touchscreen region 9632a and the touchscreen region 9632b at the same time.

The display mode switch 9034 can switch the display between a portrait mode, a landscape mode, and the like, and between monochrome display and color display, for example. With the power saver switch 9036, the luminance of display can be optimized in accordance with the amount of external light at the time when the tablet terminal is in use, which is detected with an optical sensor incorporated in the tablet terminal. The tablet terminal may include another sensing device such as a sensor for determining inclination (e.g., a gyroscope or an acceleration sensor) in addition to the optical sensor.

Although FIG. 12A illustrates an example in which the display portion 9631a and the display portion 9631b have the same display area, one embodiment of the present invention is not limited to the example. The display portion 9631a and the display portion 9631b may have different display areas and different display quality. For example, one of them may be a display panel that can display higher-definition images than the other.

The tablet terminal is folded in FIG. 12B. The tablet terminal includes the housing 9630, a solar cell 9633, a charge and discharge control circuit 9634, a battery 9635, and a DC-to-DC converter 9636. Note that FIG. 12B illustrates an example in which the charge and discharge control circuit 9634 includes the battery 9635 and the DC-to-DC converter 9636.

Since the tablet terminal can be folded, the housing 9630 can be closed when not in use. Thus, the display portions 9631a and 9631b can be protected, thereby providing a tablet terminal with excellent durability and excellent reliability for long-term use.

In addition, the tablet terminal illustrated in FIGS. 12A and 12B can have a function of displaying various kinds of information (e.g., a still image, a moving image, and a text image) on the display portion, a function of displaying a calendar, the date, the time, or the like on the display portion, a touch input function of operating or editing information displayed on the display portion by touch input, a function of controlling processing by various kinds of software (programs), and the like.

The solar cell 9633, which is attached on the surface of the tablet terminal, supplies electric power to a touchscreen, a display portion, an image signal processor, and the like. Note that the solar cell 9633 is preferably provided on one or two surfaces of the housing 9630, in which case the battery 9635 can be charged efficiently.

Figure 12C:
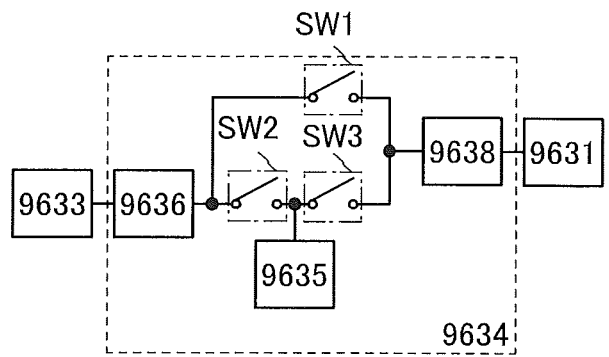

The structure and operation of the charge and discharge control circuit 9634 illustrated in FIG. 12B are described with reference to a block diagram of FIG. 12C. FIG. 12C shows the solar cell 9633, the battery 9635, the DC-to-DC converter 9636, a converter 9638, switches SW1 to SW3, and the display portion 9631. The battery 9635, the DC-to-DC converter 9636, the converter 9638, and the switches SW1 to SW3 correspond to the charge and discharge control circuit 9634 in FIG. 12B.

First, an example of operation in the case where power is generated by the solar cell 9633 using external light is described. The voltage of power generated by the solar cell is raised or lowered by the DC-to-DC converter 9636 so that the power has voltage for charging the battery 9635. Then, when power supplied from the solar cell 9633 is used for the operation of the display portion 9631, the switch SW1 is turned on and the voltage of the power is raised or lowered by the converter 9638 so as to be voltage needed for the display portion 9631. In addition, when display on the display portion 9631 is not performed, the switch SW1 is turned off and the switch SW2 is turned on so that charge of the battery 9635 may be performed.

Although the solar cell 9633 is described as an example of a power generation unit, the power generation unit is not particularly limited, and the battery 9635 may be charged by another power generation unit such as a piezoelectric element or a thermoelectric conversion element (Peltier element). The battery 9635 may be charged by a non-contact power transmission module which is capable of charging by transmitting and receiving power by wireless (without contact), or any of the other charge unit used in combination, and the power generation unit is not necessarily provided.

One embodiment of the present invention is not limited to the tablet terminal having the shape illustrated in FIGS. 12A to 12C as long as the display portion 9631 is included.

Figure 9B:
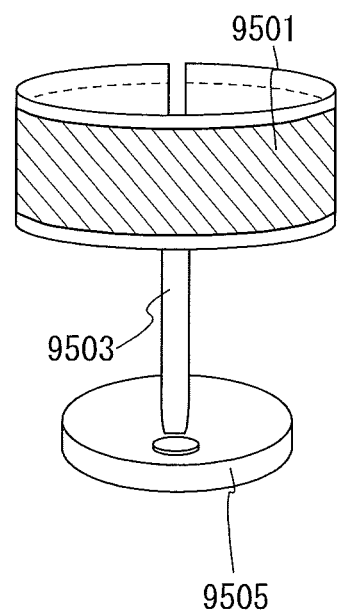

Another example of the lighting device is illustrated in FIG. 9B. A desk lamp illustrated in FIG. 9B includes a lighting portion 9501, a support 9503, a support base 9505, and the like. The lighting portion 9501 includes the light-emitting element of one embodiment of the present invention. By thus fabricating a light-emitting element of one embodiment of the present invention over a flexible substrate, a lighting device having a curved surface or having a flexible lighting portion can be provided. The use of a flexible light-emitting device for a lighting device as described above not only improves the degree of freedom in design of the lighting device but also enables the lighting device to be mounted on a portion having a curved surface, such as the ceiling or dashboard of an automobile.

As described above, by applying the light-emitting element of one embodiment of the present invention, a lighting device can realize high emission efficiency. By applying one embodiment of the present invention, a lighting device with high reliability can be provided. By applying one embodiment of the present invention, a lighting device with low power consumption can be provided.

As described above, electronic devices or lighting devices can be obtained by application of the light-emitting element. The light-emitting element has a considerably wide application range, and can be applied to electronic devices in a variety of fields.

Note that the structure described in this embodiment can be combined as appropriate with any of the structures described in the other embodiments.

Example 1

Reference Example

In this reference example, a synthesis example of 4-{3-[3'-(9H-carbazol-9-yl)]biphenyl-3-yl}benzofuro[3,2-d]pyrimidine (abbreviation: 4mCzBPBfpm) (structural formula (100)) that is a compound having the benzofuropyrimidine skeleton and described in Embodiment 1 will be specifically described. The structural formula of 4mCzBPBfpm is shown below.

[Chemical formula 11]

(100)

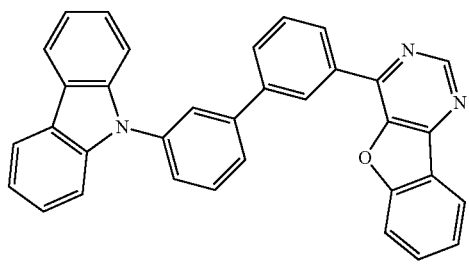

Step 1: Synthesis of
9-[3-(3-bromophenyl)phenyl]-9H-carbazole

First, 16 g (56 mmol) of 3-(9H-carbazol-9-yl)phenylboronic acid, 19 g (67 mmol) of 3-iodobromobenzene, 0.68 g (2.2 mmol) of tri(ortho-tolyl)phosphine, 56 mL of a 2 M aqueous solution of potassium carbonate, 250 mL of toluene, and 30 mL of ethanol were put into a 1-L three-neck flask, and the air in the flask was replaced with nitrogen. To this mixture was added 0.13 g (0.56 mmol) of palladium acetate, and the mixture was heated and stirred at 80° C. for 14 hours. The aqueous layer of the obtained reaction mixture was subjected to extraction with toluene, and the solution of the extract and the organic layer were combined and washed with water and a saturated aqueous solution of sodium chloride. Magnesium sulfate was added to the organic layer for drying, and the resulting mixture was subjected to gravity filtration to give a filtrate. This filtrate was concentrated to give an oily substance. The oily substance was purified by recycling preparative HPLC using LC-SakuraNEXT. The resulting fraction was concentrated and washed with toluene and methanol; thus, 9-[3-(3-bromophenyl)phenyl]-9H-carbazole was obtained as 13 g of a white solid in a yield of 58%. The synthesis scheme of the step 1 is shown in (a-2) below.

[Chemical formula 12]

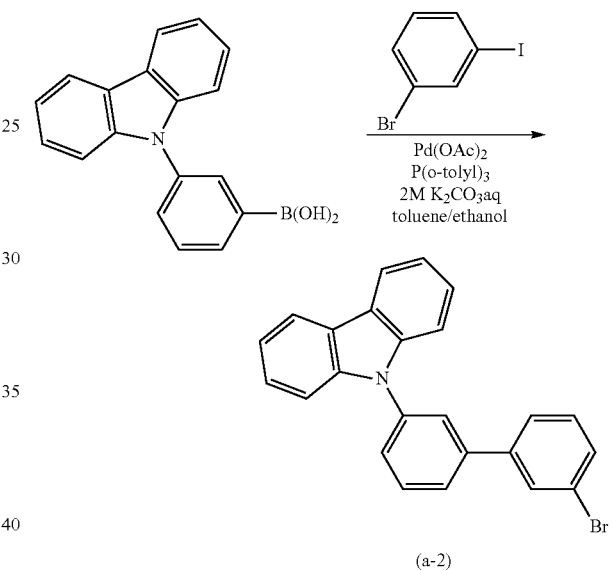

(a-2)

Step 2: Synthesis of 3-[3'-(9H-carbazol-9-yl)]biphenylboronic acid

In a 500-mL three-neck flask was put 13 g (33 mmol) of 9-[3-(3-bromophenyl)phenyl]-9H-carbazole, the flask was degassed, and the air in the flask was replaced with nitrogen. Then, 160 mL of tetrahydrofuran was added and stirring was performed at −78° C. To this mixed solvent, 24 mL (40 mmol) of n-butyl lithium (1.65 mol/L hexane solution) was dropped and stirring was performed at −78° C. for 1 hour. After the predetermined time elapsed, 4.7 mL (43 mmol) of trimethyl borate was added to this mixed solution, and stirring was performed for 18 hours while the temperature was raised to 20° C. After the predetermined time elapsed, 100 mL of 1 mol/L hydrochloric acid was added to the reaction solution, and stirring was performed at room temperature for 30 minutes. The aqueous layer of this mixture was subjected to extraction with ethyl acetate, and the solution of the extract was washed with a saturated aqueous solution of sodium chloride. Anhydrous magnesium sulfate was added to the organic layer for drying, and the resulting mixture was subjected to gravity filtration. The filtrate was concentrated to give a solid. This solid was washed with toluene, so that 3-[3'-(9H-carbazol-9-yl)]biphenylboronic acid was obtained as 6.0 g of a white solid in a yield of 51%. The synthesis scheme of the step 2 is shown in (b-2) below.

[Chemical formula 13]

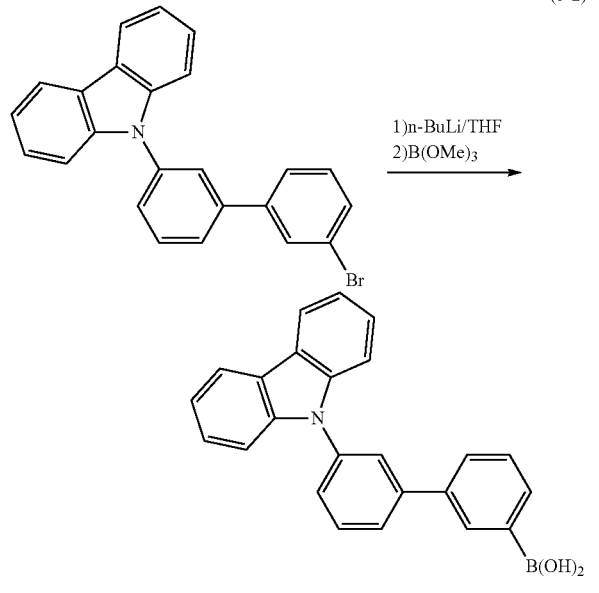

Step 3: Synthesis of 4-{3-[3'-(9H-carbazol-9-yl)]biphenyl-3-yl}benzofuro[3,2-d]pyrimidine (abbreviation: 4mCzBPBfpm)

In a 200-mL three-neck flask were put 3.0 g (8.3 mmol) of 3-[3'-(9H-carbazol-9-yl)]biphenylboronic acid, 1.7 g (8.3 mmol) of 4-chlorobenzofuro[3,2-d]pyrimidine, 8.3 mL of a 2 M aqueous solution of potassium carbonate, 40 mL of toluene, and 4 mL of ethanol, and the air in the flask was replaced with nitrogen. To this mixture was added 68.3 mg (0.059 mmol) of bis(triphenylphosphine)palladium(II) dichloride (Pd(PPh$_3$)$_2$Cl$_2$), and the mixture was heated and stirred at 80° C. for 6 hours. The aqueous layer of the obtained reaction solution was subjected to extraction with toluene, and the solution of the extract and the organic layer were combined and washed with a saturated aqueous solution of sodium chloride. Anhydrous magnesium sulfate was added to the organic layer for drying, and the resulting mixture was subjected to gravity filtration to give a filtrate. The filtrate was concentrated to give a solid. The solid was dissolved in toluene and this solution was filtered through Celite (produced by Wako Pure Chemical Industries, Ltd., Catalog No. 531-16855), alumina, and Celite. The filtrate was concentrated to give a solid. The solid was recrystallized from toluene, so that 2.0 g of a white solid was obtained in a yield of 50%. Then, 2.0 g of the white solid was purified by sublimation using a train sublimation method. The sublimation purification was conducted under the conditions where the pressure was 2.3 Pa, the flow rate of an argon gas was 10 mL/min, and the solid was heated at 250° C. After the sublimation purification, 1.3 g of a white solid which was a target substance was obtained at a collection rate of 65%. The synthesis scheme of the step 3 is shown in (c-2) below.

[Chemical formula 14]

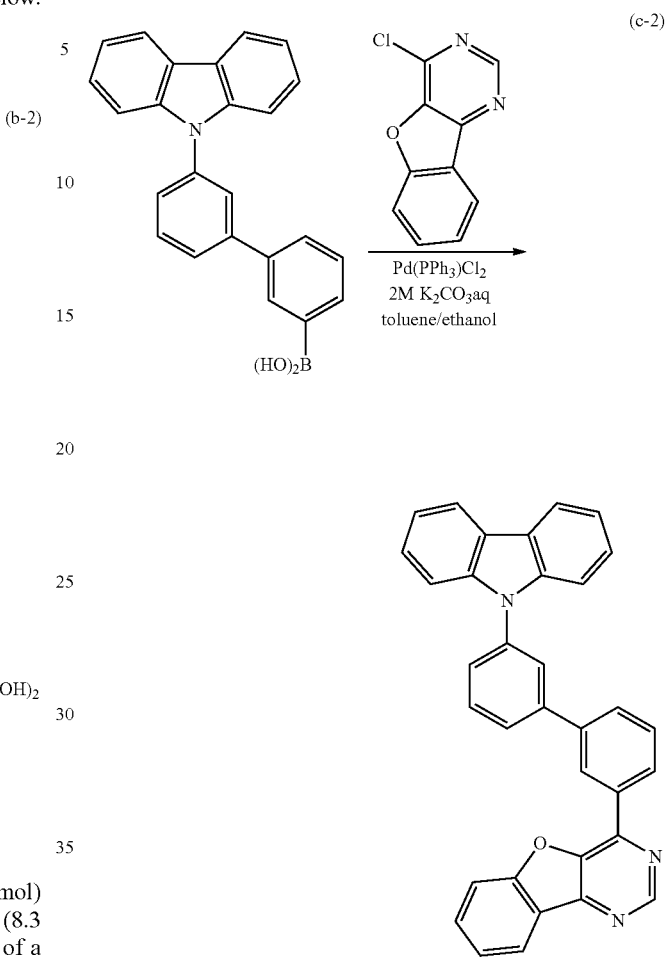

Analysis results by nuclear magnetic resonance ($^1$H-NMR) spectroscopy of the white solid obtained in the step 3 are described below. The measurement results reveal that 4mCzBPBfpm, which was the target substance, was obtained.

$^1$H-NMR. δ(CDCl$_3$): 7.32 (m, 2H), 7.44 (m, 2H), 7.52-7.55 (m, 3H), 7.63-7.64 (m, 1H), 7.69-7.77 (m, 4H), 7.85-7.88 (m, 2H), 7.97 (t, 1H), 8.18 (d, 2H), 8.31 (d, 1H), 8.65 (m, 1H), 8.92 (t, 1H), 9.27 (s, 1H).

<<Light-Emitting Element 1 and Comparative Light-Emitting Element 1>>

Next, a light-emitting element (light-emitting element 1) of one embodiment of the present invention and a comparative light-emitting element (comparative light-emitting element 1) are described. Note that as the second organic compound in the light-emitting layer 113, 4mCzBPBfpm (structural formula (100)) was used in the light-emitting element 1 and 4-[3'-(dibenzothiophen-4-yl)biphenyl-3-yl]benzofuro[3,2-d]pyrimidine (abbreviation: 4mDBTBPBfpm-II) (structural formula (v)) was used in the comparative light-emitting element 1.

The molecular structures of compounds used in this example are shown in structural formulae (i) to (v) and (100) below. The element structure in FIG. 1A was employed.

[Chemical formulae 15]

(i)

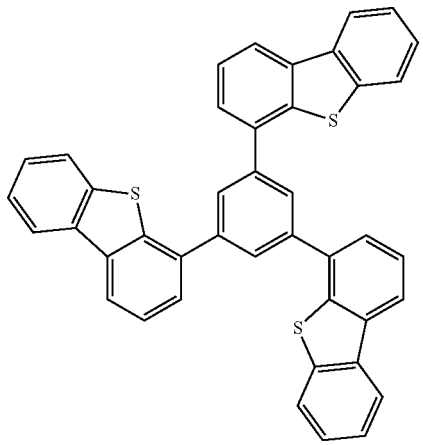

DBT3P-II (ii)

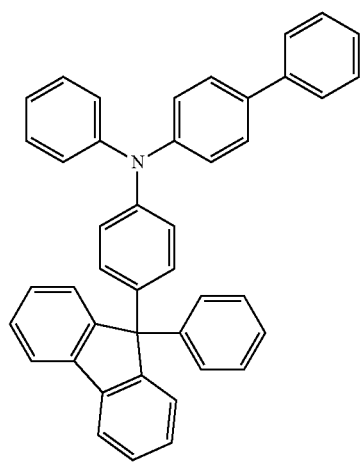

BPAFLP (iv)

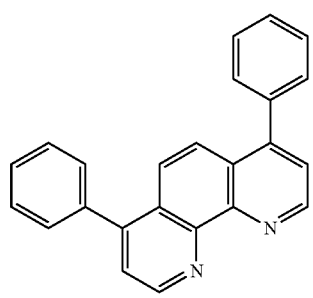

BPhen (iii)

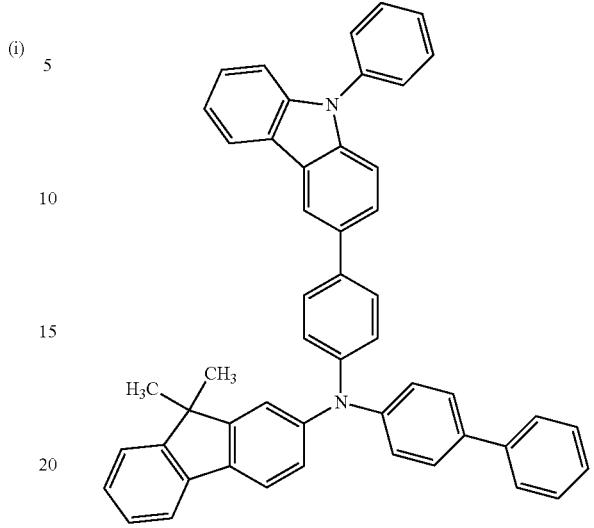

PCBBiF (100)

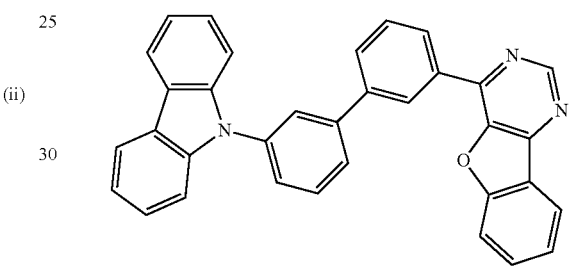

(v)

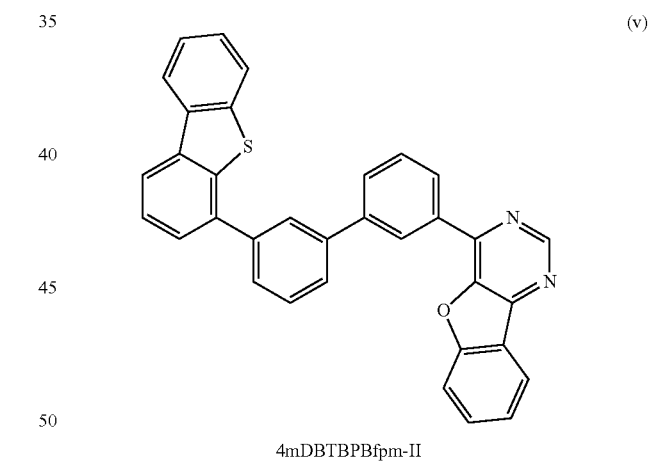

4mDBTBPBfpm-II

<<Fabrication of Light-Emitting Element 1>>

First, a glass substrate, over which a film of indium tin oxide containing silicon (ITSO) was formed to a thickness of 70 nm as the first electrode 101, was prepared. A surface of the ITSO was covered with a polyimide film so that an area of 2 mm×2 mm of the surface was exposed. The electrode area was 2 mm×2 mm. As pretreatment for forming the light-emitting element over the substrate, the surface of the substrate was washed with water and baked at 200° C. for 1 hour, and then a UV ozone treatment was performed for 370 seconds. Then, the substrate was transferred into a vacuum evaporation apparatus where the pressure was reduced to about $10^{-4}$ Pa, vacuum baking at 170° C. for 30 minutes was performed in a heating chamber of the vacuum evaporation apparatus, and then the substrate was cooled down for about 30 minutes.

Then, the substrate was fixed to a holder provided in the vacuum evaporation apparatus such that the surface of the substrate over which the first electrode 101 was formed faced downward. In this example, a case is described in which the hole-injection layer 111, the hole-transport layer 112, the light-emitting layer 113, the electron-transport layer 114, and the electron-injection layer 115, which were included in the layer 103 containing an organic compound, were sequentially formed by a vacuum evaporation method.

After reducing the pressure in the vacuum evaporation apparatus to $10^{-4}$ Pa, 4,4',4''-(benzene-1,3,5-triyl)tri(dibenzothiophene) (abbreviation: DBT3P-II) (structural formula (i)) and molybdenum oxide were deposited by co-evaporation such that the mass ratio of DBT3P-II to molybdenum oxide was 2:1, whereby the hole-injection layer 111 was formed over the first electrode 101. The thickness was set to 60 nm. Note that a co-evaporation method is an evaporation method in which a plurality of different substances is concurrently vaporized from respective different evaporation sources.

Next, 4-phenyl-4'-(9-phenylfluoren-9-yl)triphenylamine (abbreviation: BPAFLP) (structural formula (ii)) was evaporated to a thickness of 20 nm, thereby forming the hole-transport layer 112.

Next, the light-emitting layer 113 was formed over the hole-transport layer 112.

The light-emitting layer 113 was formed in the following manner: 4-{3-[3'-(9H-carbazol-9-yl)]biphenyl-3-yl}benzofuro[3,2-d]pyrimidine (abbreviation: 4mCzBPBfpm) (structural formula (100)) and N-(1,1'-biphenyl-4-yl)-N-[4-(9-phenyl-9H-carbazol-3-yl)phenyl]-9,9-dimethyl-9H-fluoren-2-amine (abbreviation: PCBBiF) (structural formula (iii)) were deposited by co-evaporation to a thickness of 40 nm such that the mass ratio of 4mCzBPBfpm to PCBBiF was 0.8:0.2, and then, 4-{3-[3'-(9H-carbazol-9-yl)]biphenyl-3-yl}benzofuro[3,2-d]pyrimidine (abbreviation: 4mCzBPBfpm) (structural formula (100)) was deposited to have a thickness of 20 nm.

Next, the electron-transport layer 114 was formed over the light-emitting layer 113. Bathophenanthroline (abbreviation: BPhen) (structural formula (iv)) was deposited by evaporation to a thickness of 10 nm, so that the electron-transport layer 114 was formed.

Next, lithium fluoride was deposited by evaporation to a thickness of 1 nm over the electron-transport layer 114, whereby the electron-injection layer 115 was formed.

Finally, aluminum was deposited by evaporation to a thickness of 200 nm over the electron-injection layer 115 to form the second electrode 102 serving as a cathode; thus, the light-emitting element 1 was obtained. It is to be noted that an evaporation method using resistive heating was employed for all the evaporation steps.

Through the above steps, the light-emitting element 1 was obtained.

<<Fabrication of Comparative Light-Emitting Element 1>>

Next, a fabrication method of the comparative light-emitting element 1 is described.

For the comparative light-emitting element 1, refer also to the fabrication method of the light-emitting element 1, since films other than the light-emitting layer 113 were formed using the same materials as those in the light-emitting element 1. The first electrode 101 of the comparative light-emitting element 1 was formed using ITSO to a thickness of 110 nm. The hole-injection layer 111 was formed by co-evaporation to a thickness of 20 nm so that the mass ratio of DBT3P-II to molybdenum oxide was 2:1. As the hole-transport layer 112, BPAFLP was deposited to a thickness of 20 nm. The light-emitting layer 113 was formed in the following manner: 4-[3'-(dibenzothiophen-4-yl)biphenyl-3-yl]benzofuro[3,2-d]pyrimidine (abbreviation: 4mDBTBPBfpm-II) (structural formula (v)) and PCBBiF were deposited by co-evaporation to a thickness of 40 nm such that the mass ratio of 4mDBTBPBfpm-II to PCBBiF was 0.8:0.2, and then, 4mDBTBPBfpm-II was deposited to a thickness of 10 nm. Next, BPhen was deposited by evaporation to a thickness of 15 nm, so that the electron-transport layer 114 was formed. The electron-injection layer 115 and the second electrode 102 were formed using the same materials and to the same thicknesses as those of the light-emitting element 1.

Element structures of the light-emitting element 1 and the comparative light-emitting element 1 obtained as described above are shown in Table 1.

TABLE 1

| | First electrode 101 | Hole-injection layer 111 | Hole-transport layer 112 | Light-emitting layer 113 | Electron-transport layer 114 | Electron-injection layer 115 | Second electrode 102 |
|---|---|---|---|---|---|---|---|
| Light-emitting element 1 | ITSO (70 nm) | DBT3P-II:MoO$_x$ (2:1 60 nm) | BPAFLP (20 nm) | *1 | BPhen (10 nm) | LiF (1 nm) | Al (200 nm) |
| Comparative light-emitting element 1 | ITSO (110 nm) | DBT3P-II:MoO$_x$ (2:1 20 nm) | | *2 | BPhen (15 nm) | | |

*1 4mCzBPBfpm:PCBBiF (0.8:0.2 40 nm)\4mCzBPBfpm (20 nm)
*2 4mDBTBPBfpm-II:PCBBiF (0.8:0.240 nm)\4mDBTBPBfpm-II (10 nm)

<<Operation Characteristics of Light-Emitting Element 1 and Comparative Light-Emitting Element 1>>

Figure 13:
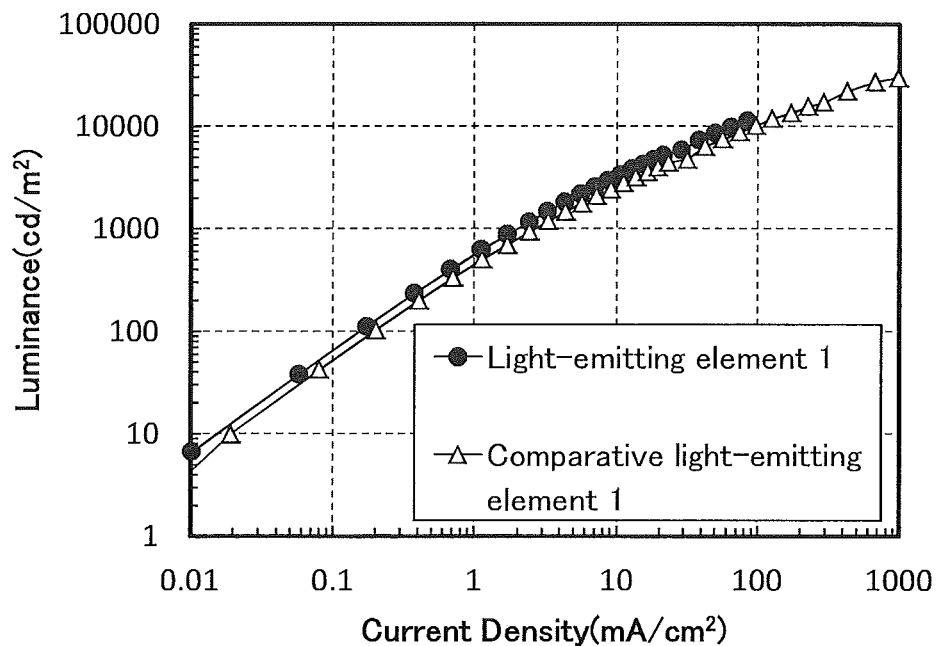
FIG. 13 shows current density-luminance characteristics of a light-emitting element 1 and a comparative light-emitting element 1.
Figure 14:
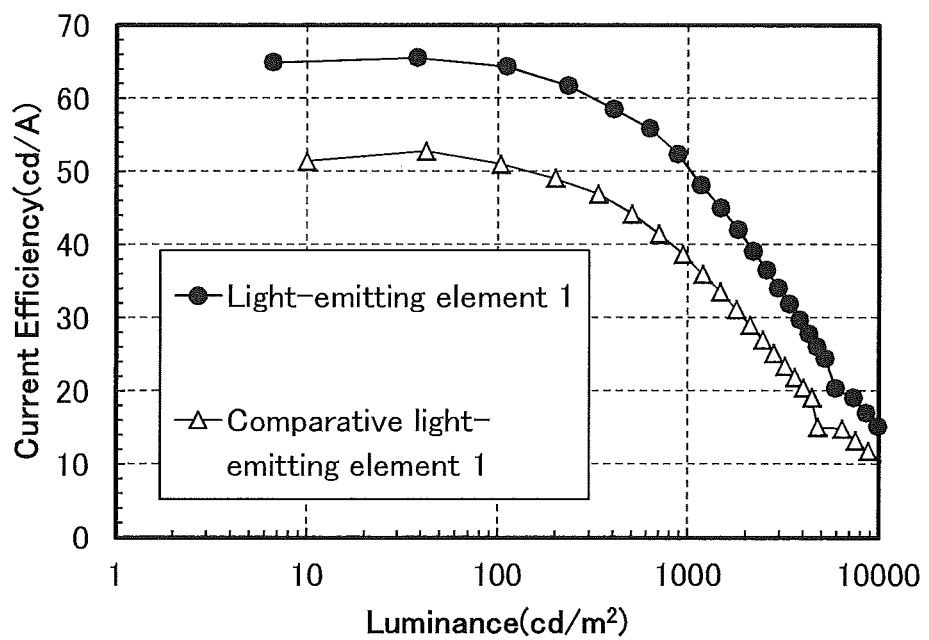
FIG. 14 shows luminance-current efficiency characteristics of the light-emitting element 1 and the comparative light-emitting element 1.
Figure 15:
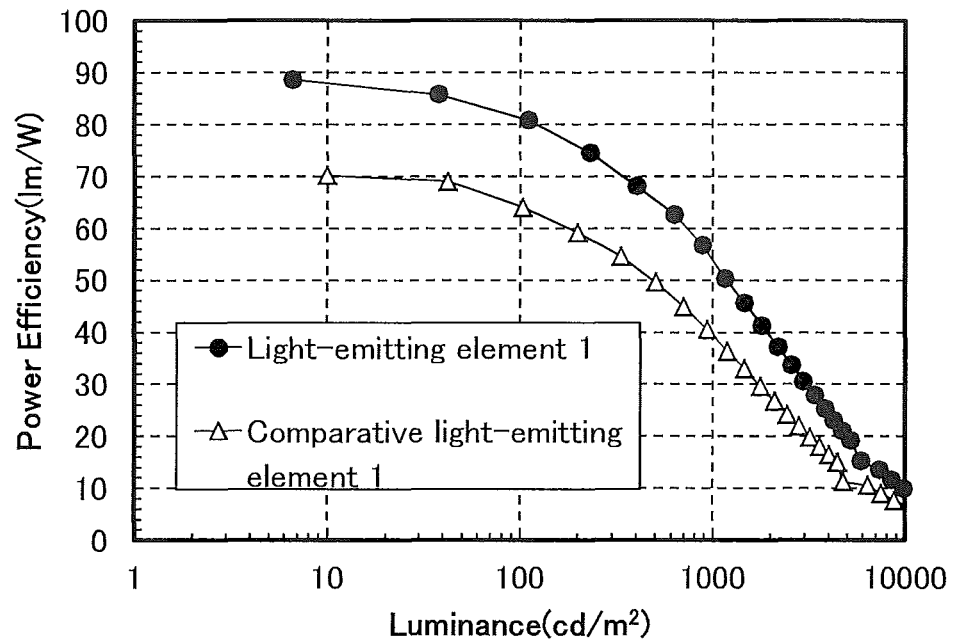
FIG. 15 shows luminance-power efficiency characteristics of the light-emitting element 1 and the comparative light-emitting element 1.
Figure 16:
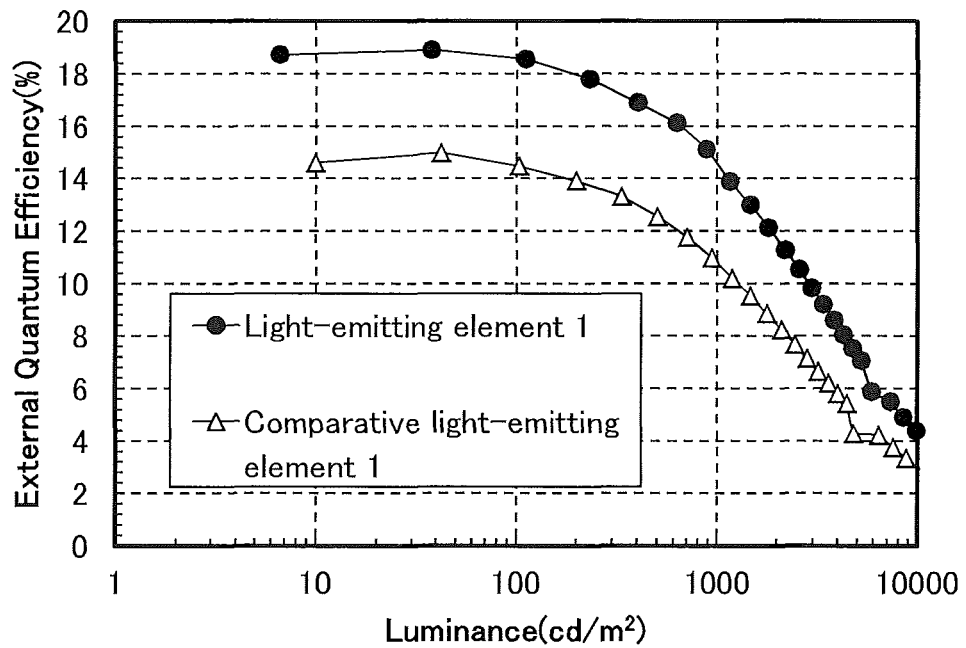
FIG. 16 shows luminance-external quantum efficiency characteristics of the light-emitting element 1 and the comparative light-emitting element 1.
Figure 17:
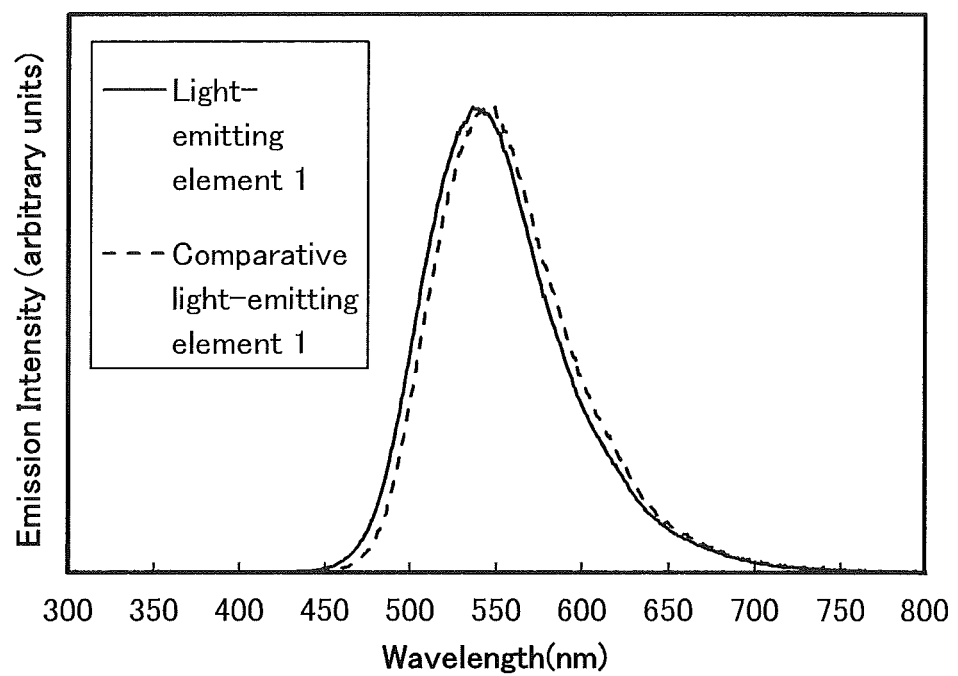
FIG. 17 shows emission spectra of the light-emitting element 1 and the comparative light-emitting element 1.

The emission characteristics of the light-emitting elements at a luminance around 900 cd/m² are shown below in Table 2. FIG. 13 shows current density-luminance characteristics of the light-emitting elements; FIG. 14 shows luminance-current efficiency characteristics of the light-emitting elements; FIG. 15 shows luminance-power efficiency characteristics of the light-emitting elements; FIG. 16 shows luminance-external quantum efficiency characteristics of the light-emitting elements; and FIG. 17 shows emission spectra.

TABLE 2

|  | Voltage (V) | Current (mA) | Current density (mA/cm²) | Chromaticity (x, y) | Luminance (cd/m²) | Current efficiency (cd/A) | Power efficiency (lm/W) | External quantum efficiency (%) |
| --- | --- | --- | --- | --- | --- | --- | --- | --- |
| Light-emitting element 1 | 2.9 | 0.068 | 1.69 | (0.38, 0.58) | 890 | 52.4 | 56.7 | 15.1 |
| Comparative light-emitting element 1 | 3.0 | 0.097 | 2.43 | (0.37, 0.59) | 940 | 38.7 | 40.5 | 11.0 |

As shown in FIG. 14 and FIG. 16, the light-emitting element 1 has more favorable luminance-current efficiency characteristics and luminance-external quantum efficiency characteristics than the comparative light-emitting element 1, which indicates that the light-emitting element 1 has high emission efficiency (high current efficiency and high external quantum efficiency). Moreover, the drive voltage of the light-emitting element 1 was low, and as a result, extremely high power efficiency as shown in FIG. 15 was achieved. Note that the difference between 4mCzBPBfpm used in the light-emitting element 1 and 4mDBTBPBfpm-II used in the comparative light-emitting element 1 is whether a carbazole skeleton or a dibenzothiophene skeleton is used. In other words, for high efficiency, it is indispensable to have not only a benzofuropyrimidine skeleton but both a carbazole skeleton and a benzofuropyrimidine skeleton, which are inseparable components for the effect of one embodiment of the present invention.

The triplet excitation level (T1 level) of 4mCzBPBfpm is estimated to be 2.68 eV (462 nm) from a phosphorescence spectrum peak at 10K. The T1 level of PCBBiF is estimated to be 2.44 eV (509 nm) in the same measurement. The T1 levels of 4mCzBPBfpm and PCBBiF are both higher than 2.26 eV (549 nm) which is the emission energy (singlet excitation level; S1 level) of the exciplex. Since the S1 level and the T1 level of the exciplex are at almost the same level, it is found from the above result that the triplet excitation energy levels (T1 levels) of the first organic compound and the second organic compound are higher than the triplet excitation energy level (T1 level) of the exciplex.

The structure described in this example can be combined with any of the other embodiments as appropriate.

REFERENCE NUMERALS

101: first electrode, 102: second electrode, 103: layer containing an organic compound, 111: hole-injection layer, 112: hole-transport layer, 113: light-emitting layer, 114: electron-transport layer, 115: electron-injection layer, 400: substrate, 401: first electrode, 402: black layer (black matrix), 403: layer containing an organic compound, 404: second electrode, 405: sealing material, 407: sealing substrate, 408: space, 412: pad, 420: IC chip, 501: first electrode, 502: second electrode, 511: first light-emitting unit, 512: second light-emitting unit, 513: charge-generation layer, 601: driver circuit portion (source line driver circuit), 602: pixel portion, 603: driver circuit portion (gate line driver circuit), 604: sealing substrate, 605: sealing material, 607: space, 608: wiring, 609: FPC (flexible printed circuit), 610: element substrate, 611: switching transistor, 612: current controlling transistor, 613: first electrode, 614: insulator, 616: layer containing an organic compound, 617: second electrode, 618: light-emitting element, 623: n-channel transistor, 624: p-channel transistor, 625: desiccant, 901: housing, 902: liquid crystal layer, 903: backlight unit, 904: housing, 905: driver IC, 906: terminal, 951: substrate, 952: electrode, 953: insulating layer, 954: partition layer, 955: layer containing an organic compound, 956: electrode, 1001: substrate, 1002: base insulating film, 1003: gate insulating film, 1006: gate electrode, 1007: gate electrode, 1008: gate electrode, 1020: first interlayer insulating film, 1021: second interlayer insulating film, 1022: electrode, 1024W: first electrode of a light-emitting element, 1024R: first electrode of a light-emitting element, 1024G: first electrode of a light-emitting element, 1024B: first electrode of a light-emitting element, 1025: partition, 1028: layer containing an organic compound, 1029: second electrode of a light-emitting element, 1031: sealing substrate, 1032: sealing material, 1033: transparent base material, 1036: overcoat layer, 1034R: red coloring layer, 1034G: green coloring layer, 1034B: blue coloring layer, 1035: black layer (black matrix), 1037: third interlayer insulating film, 1040: pixel portion, 1041: driver circuit portion, 1042: peripheral portion, 2001: housing, 2002: light source, 3001: lighting device, 5000: display region, 5001: display region, 5002: display region, 5003: display region, 5004: display region, 5005: display region, 7101: housing, 7103: display portion, 7105: stand, 7107: display portion, 7109: operation key, 7110: remote controller, 7201: main body, 7202: housing, 7203: display portion, 7204: keyboard, 7205: external connection port, 7206: pointing device, 7210: second display portion, 7301: housing, 7302: housing, 7303: joint portion, 7304: display portion, 7305: display portion, 7306: speaker portion, 7307: recording medium insertion portion, 7308: LED lamp, 7309: operation key, 7310: connection terminal, 7311: sensor, 7401: housing, 7402: display portion, 7403: operation button, 7404: external connection port, 7405: speaker, 7406: microphone, 9033: clasp, 9034: switch, 9035: power switch, 9036: switch, 9038: operation switch, 9501: lighting portion, 9503: support, 9505: support base, 9630: housing, 9631: display portion, 9631a: display portion, 9631b: display portion, 9632a: touchscreen region, 9632b: touchscreen region, 9633: solar cell, 9634: charge and discharge control circuit, 9635: battery, 9636: DC-to-DC converter, 9637: operation key, 9638: converter, and 9639: button.

This application is based on Japanese Patent Application serial no. 2015-109756 filed with Japan Patent Office on May 29, 2015, the entire contents of which are hereby incorporated by reference.

The invention claimed is:
1. A light-emitting element comprising:
a first electrode;
a second electrode; and
a light-emitting layer between the first electrode and the second electrode,
wherein the light-emitting layer consists of a first organic compound and a second organic compound, wherein the second organic compound comprises a first carbazole skeleton and a substituted or unsubstituted first bivalent aromatic hydrocarbon group, wherein the first carbazole skeleton is bonded to the first bivalent aromatic hydrocarbon group, wherein the second organic compound further comprises a benzofuro[3,2-d]pyrimidine skeleton or a benzothieno[3,2-d]pyrimidine skeleton, wherein the first bivalent aromatic hydrocarbon group is bonded to the benzofuro[3,2-d]pyrimidine skeleton or the benzothieno[3,2-d]pyrimidine skeleton, wherein the first organic compound and the second organic compound form an exciplex, wherein light emitted from the light-emitting layer comprises light emitted from the exciplex, and wherein the first organic compound comprises a second carbazole skeleton and an aromatic amine skeleton.

2. The light-emitting element according to claim 1, wherein the first bivalent aromatic hydrocarbon group comprises 6 to 60 carbon atoms.

3. The light-emitting element according to claim 1, wherein the first bivalent aromatic hydrocarbon group comprises 6 to 13 carbon atoms.

4. The light-emitting element according to claim 1, wherein the first bivalent aromatic hydrocarbon group comprises a biphenyldiyl group.

5. The light-emitting element according to claim 4, wherein the biphenyldiyl group is a 3,3'-biphenyldiyl group.

6. The light-emitting element according to claim 1, wherein the second organic compound is an organic compound represented by a structural formula (100) or (200),

[Chemical formula 1]

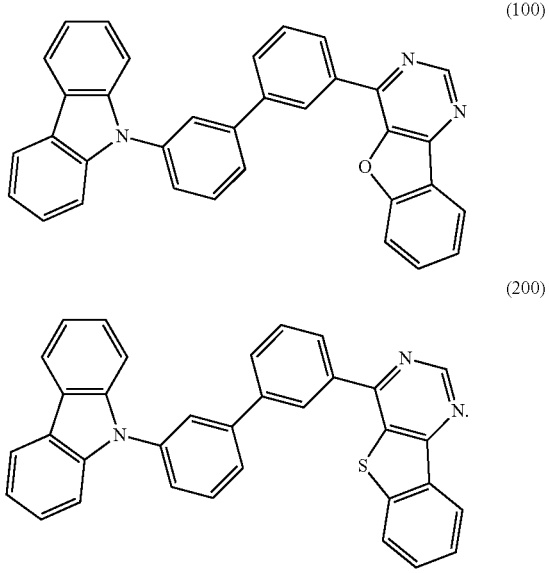

(100)

(200)

7. The light-emitting element according to claim 1, wherein the second organic compound has an electron-transport property and the first organic compound has a hole-transport property.

8. The light-emitting element according to claim 1, wherein triplet excitation energy levels of the first organic compound and the second organic compound are higher than a triplet excitation energy level of the exciplex.

9. The light-emitting element according to claim 1, wherein light emission comprises a delayed fluorescence component.

10. A lighting device comprising:
the light-emitting element according to claim 1; and
a switch.

11. A light-emitting device comprising:
the light-emitting element according to claim 1; and
a unit configured to control the light-emitting element.

12. A display device comprising:
the light-emitting element according to claim 1 in a display portion; and
a unit configured to control the light-emitting element.

13. An electronic device comprising:
the light-emitting element according to claim 1; and
a switch.

14. A light-emitting element comprising:
a first electrode;
a second electrode; and
an emission layer between the first electrode and the second electrode,
wherein the layer consists of a first organic compound and a second organic compound,
wherein the second organic compound comprises a first carbazole skeleton and a substituted or unsubstituted first bivalent aromatic hydrocarbon group,
wherein the second organic compound further comprises a benzofuropyrimidine skeleton or a benzothienopyrimidine skeleton,
wherein the first carbazole skeleton is bonded to the first bivalent aromatic hydrocarbon group,
wherein the first bivalent aromatic hydrocarbon group is bonded to the benzofuropyrimidine skeleton or the benzothienopyrimidine skeleton,
wherein the first organic compound and the second organic compound faun an exciplex,
wherein light emitted from the light-emitting layer comprises light emitted from the exciplex,
wherein the exciplex emits green light, and
wherein the first organic compound comprises a second carbazole skeleton and an aromatic amine skeleton.

15. The light-emitting element according to claim 14, wherein the first bivalent aromatic hydrocarbon group comprises 6 to 60 carbon atoms.

16. The light-emitting element according to claim 14, wherein the first bivalent aromatic hydrocarbon group comprises 6 to 13 carbon atoms.

17. The light-emitting element according to claim 14, wherein the first bivalent aromatic hydrocarbon group comprises a biphenyldiyl group.

18. The light-emitting element according to claim 17, wherein the biphenyldiyl group is a 3,3'-biphenyldiyl group.

19. The light-emitting element according to claim 14, wherein the second organic compound has an electron-transport property and the first organic compound has a hole-transport property.

20. The light-emitting element according to claim 14, wherein triplet excitation energy levels of the first organic compound and the second organic compound are higher than a triplet excitation energy level of the exciplex.

21. The light-emitting element according to claim 14, wherein light emission comprises a delayed fluorescence component.

22. A lighting device comprising:
the light-emitting element according to claim 14; and
a switch.

23. A light-emitting device comprising:
the light-emitting element according to claim 14; and
a unit configured to control the light-emitting element.

24. A display device comprising:
the light-emitting element according to claim 14 in a display portion; and
a unit configured to control the light-emitting element.

25. An electronic device comprising:
the light-emitting element according to claim 14; and
a switch.

26. The light-emitting element according to claim 1, wherein a the benzofuro[3,2-d]pyrimidine skeleton or the benzothieno[3,2-d]pyrimidine skeleton is bonded to the first bivalent aromatic hydrocarbon group at 4-position of the benzofuro[3,2-d]pyrimidine skeleton or the benzothieno[3,2-d]pyrimidine skeleton.

27. The light-emitting element according to claim 14, wherein the second organic compound is an organic compound represented by a structural formula (100) or (200),

[Chemical formula 1]

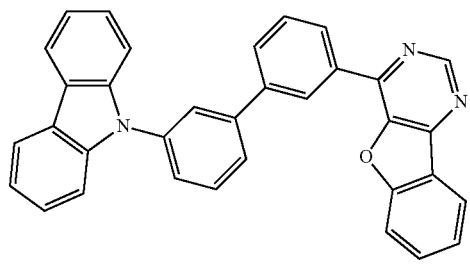
(100)

[Chemical formula 2]

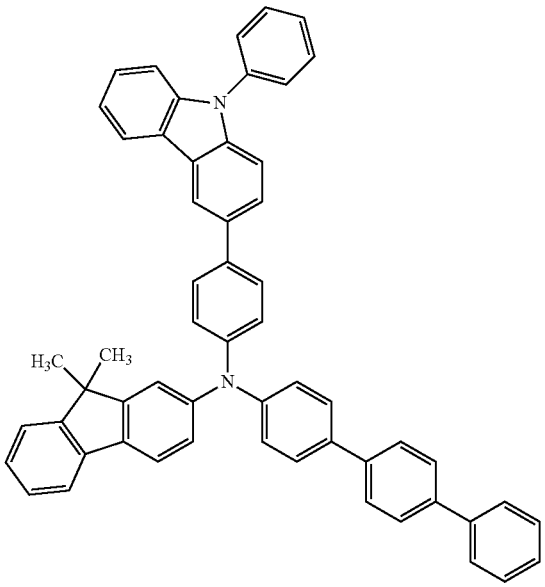
(iii)

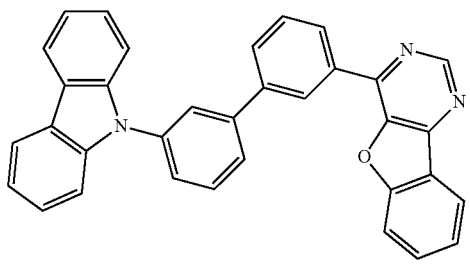
(100)

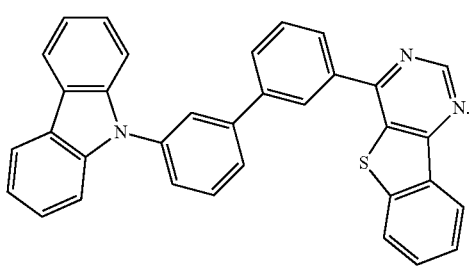
(200)

28. The light-emitting element according to claim 1, wherein the first organic compound is an organic compound represented by a structural formula (iii),
wherein the second organic compound is an organic compound represented by a structural formula (100) or (200), 29. The light-emitting element according to claim 14, wherein the first organic compound is an organic compound represented by a structural formula (iii),
wherein the second organic compound is an organic compound represented by a structural formula (100) or (200),

[Chemical formula 2]

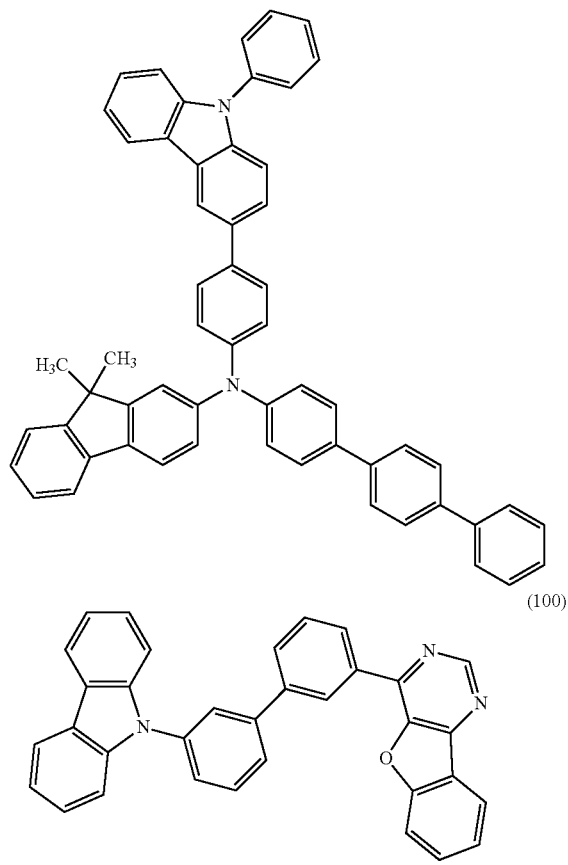

(iii)

(100)

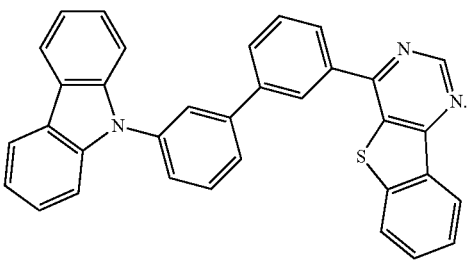

(200)

30. The light emitting element according claim 1, wherein the first organic compound further comprises a substituted or unsubstituted second bivalent aromatic hydrocarbon group,
    wherein the second bivalent aromatic hydrocarbon group is bonded to the second carbazole skeleton,
    wherein the second bivalent aromatic hydrocarbon group is bonded to the aromatic amine skeleton.

31. The light emitting element according claim 14, wherein the first organic compound further comprises a substituted or unsubstituted second bivalent aromatic hydrocarbon group,
    wherein the second bivalent aromatic hydrocarbon group is bonded to the second carbazole skeleton,
    wherein the second bivalent aromatic hydrocarbon group is bonded to the aromatic amine skeleton.

32. The light-emitting element according to claim 1, wherein the first carbazole skeleton is bonded to the first bivalent aromatic hydrocarbon group at 9-position of the first carbazole skeleton.

* * * * *